US009199005B2

(12) United States Patent
LeGeros et al.

(10) Patent No.: US 9,199,005 B2
(45) Date of Patent: *Dec. 1, 2015

(54) CALCIUM PHOSPHATE-BASED MATERIALS CONTAINING ZINC, MAGNESIUM, FLUORIDE AND CARBONATE

(75) Inventors: Racquel Z. LeGeros, New York, NY (US); John LeGeros, New York, NY (US); Dindo Mijares, Woodside, NY (US)

(73) Assignee: New York University, New York, NY (US)

(*) Notice: Subject to any disclaimer, the term of this patent is extended or adjusted under 35 U.S.C. 154(b) by 1405 days.

This patent is subject to a terminal disclaimer.

(21) Appl. No.: 12/220,520

(22) Filed: Jul. 25, 2008

(65) Prior Publication Data
US 2009/0068285 A1    Mar. 12, 2009

Related U.S. Application Data

(63) Continuation-in-part of application No. 10/952,530, filed on Sep. 28, 2004, now Pat. No. 7,419,680.

(60) Provisional application No. 60/507,593, filed on Oct. 1, 2003.

(51) Int. Cl.
| A61K 33/06 | (2006.01) |
| A61K 33/16 | (2006.01) |
| A61K 33/30 | (2006.01) |
| A61K 33/42 | (2006.01) |
| A61L 27/42 | (2006.01) |
| A61L 27/44 | (2006.01) |
| A61L 27/12 | (2006.01) |

(52) U.S. Cl.
CPC ............... *A61L 27/44* (2013.01); *A61K 33/06* (2013.01); *A61K 33/16* (2013.01); *A61K 33/30* (2013.01); *A61K 33/42* (2013.01); *A61L 27/12* (2013.01); *A61L 27/425* (2013.01)

(58) Field of Classification Search
CPC .............................. A61L 27/425; A61L 27/44
USPC .................................. 424/602, 604, 641, 682
See application file for complete search history.

(56) References Cited

U.S. PATENT DOCUMENTS

| 4,880,610 | A | 11/1989 | Constantz |
| 4,917,702 | A * | 4/1990 | Scheicher et al. ............ 424/423 |
| 4,965,088 | A | 10/1990 | Shimamune et al. |
| 5,141,576 | A | 8/1992 | Shimamune et al. |
| 5,205,921 | A | 4/1993 | Shirkanzadeh |
| 5,211,833 | A | 5/1993 | Shirkhanzadeh |
| 5,258,044 | A | 11/1993 | Lee |
| 5,279,831 | A | 1/1994 | Constantz et al. |
| 5,612,049 | A | 3/1997 | Li et al. |
| 6,037,519 | A | 3/2000 | McKay |
| 6,069,295 | A | 5/2000 | Leitao |
| 6,153,266 | A | 11/2000 | Yokogawa et al. |
| 6,207,218 | B1 | 3/2001 | Layrolle et al. |
| 6,280,789 | B1 | 8/2001 | Rey et al. |
| 6,331,312 | B1 | 12/2001 | Lee et al. |
| 6,346,123 | B1 | 2/2002 | McKay |
| 6,428,803 | B1 | 8/2002 | Ewers et al. |
| 6,585,946 | B1 | 7/2003 | Bonfield et al. |
| 7,351,280 | B2 | 4/2008 | Khairoun et al. |
| RE41,584 | E * | 8/2010 | Ying et al. .................... 501/1 |

OTHER PUBLICATIONS

HCAPLUS Abstract 1981:98396 (1981).*
Dorozhkin, S., "Biphasic, triphasic and multiphasic calcium orthophosphates," Acta Biomaterialia, available online on Nov. 20, 2011 from www.elsevier.com/locate/actabiomat; obtained online from Science Direct on Dec. 3, 2011.*
Nakamura, M. et al., "Characterization of bone mineral-resembling biomaterials for optimizing human osteoclast differentiation and resorption," Journal of Biomedical Materials Research Part A, vol. 101, pp. 3141-3151 (2013).*
Ajibola, et al., "Tranformation of amorphous calcium . . . "., Bulletin of the Chemical Society of Ethiopa, 1997, vol. 11(1) , pp. 19-24.
Webster's New World Dictionary, Simon & Schuster, Inc., New York, 1988, p. 1067.

(Continued)

Primary Examiner — John Pak
(74) Attorney, Agent, or Firm — Klauber & Jackson LLC

(57) ABSTRACT

The present invention provides novel biomaterials comprising one or more of Mg, Zn and F ions in a carbonate-containing biphasic calcium phosphate (BCP) system. The biomaterial may contain Mg, Zn, F, Mg and Zn, Mg and F, Zn and F, or Mg, Zn and F. The biomaterial may be substantially similar in composition to bone mineral (a carbonate apatite). The biomaterial may feature slow release of Mg, Zn, F, Ca, and P ions. The biphasic calcium phosphate, BCP, may be a mixture of unsubstituted hydroxyapatite (HA) and unsubstituted.-TCP, $Ca_3(PO_4)_2$. BCP of varying HA/.-TCP ratios may be produced by sintering calcium-deficient apatite, for instance having a Ca/P<1.5, 1.6, 1.67, 1.75 or 1.8 that has been prepared either by a precipitation or by a hydrolysis method or by a solid-state reaction. The amount of each component (by weight %) present in the biomaterials may be as follows: Mg 0.5 to 12 wt %, Zn 1 to 12 wt %, F 0.1 to 4 wt %, calcium 20 to 40 wt %, phosphate 10 to 20 wt %, and carbonate ($CO_3$) 1 to 20 wt %. The biomaterial may further comprise one or more other ion such as strontium, manganese, copper, boron or silicate, or one or more other organic moiety such as a protein, a peptide, or a nutraceutical which may provide antioxidant, anti-bacterial or anti-inflammatory properties. The invention also provides methods of inhibiting bone resorption, methods of treating osteoporosis or delaying the onset of osteoporosis, methods of treating a bone fracture, and methods of inhibiting osteoclast activity. Further, the invention provides methods of treating or reversing bone deficiencies such as bone loss, similar to osteoporosis, caused all or in part by a mineral deficient diet, a disease such as cancer or osteopenia, a treatment such as steroid therapy or radiation therapy, or a physical condition such as immobilization.

13 Claims, 25 Drawing Sheets

(56) References Cited

OTHER PUBLICATIONS

Genius, et al., "Picking a bone with contemporaryosteoporosis management . . . " Clinical Nutrition 26; pp. 193-207, (2007).
LeGeros, et al. "Biphasic calcium phosphate bioceramics . . . " pp. 201-209 (Mar. 2003).
Daculsi, et al, "Current state of the art of biphasic calcium phosphate bioceramics" pp. 195-200, (Mar. 2003).
Julien, et al. "Physico-chemical-mechanical and in vitro biological properties . . . " Biomaterials 28 (2007) pp. 956-965.
LeGeros, et al. Fluoride-cation interactions in the formation and stability of apatites Journal of Fluorine Chemistry, 41 (1988) pp. 53-64.
Manjubala, et al, "Preparation of biphasic calcium phosphate . . . " Journal of Material science Letters 20 pp. 1225-1227, (2001).
LeGeros, Properties of Osteocoductive Biomaterials: Calcium Phosphates, Clinical Orthopaedics . . . 395 (2002) pp. 81-98.

\* cited by examiner

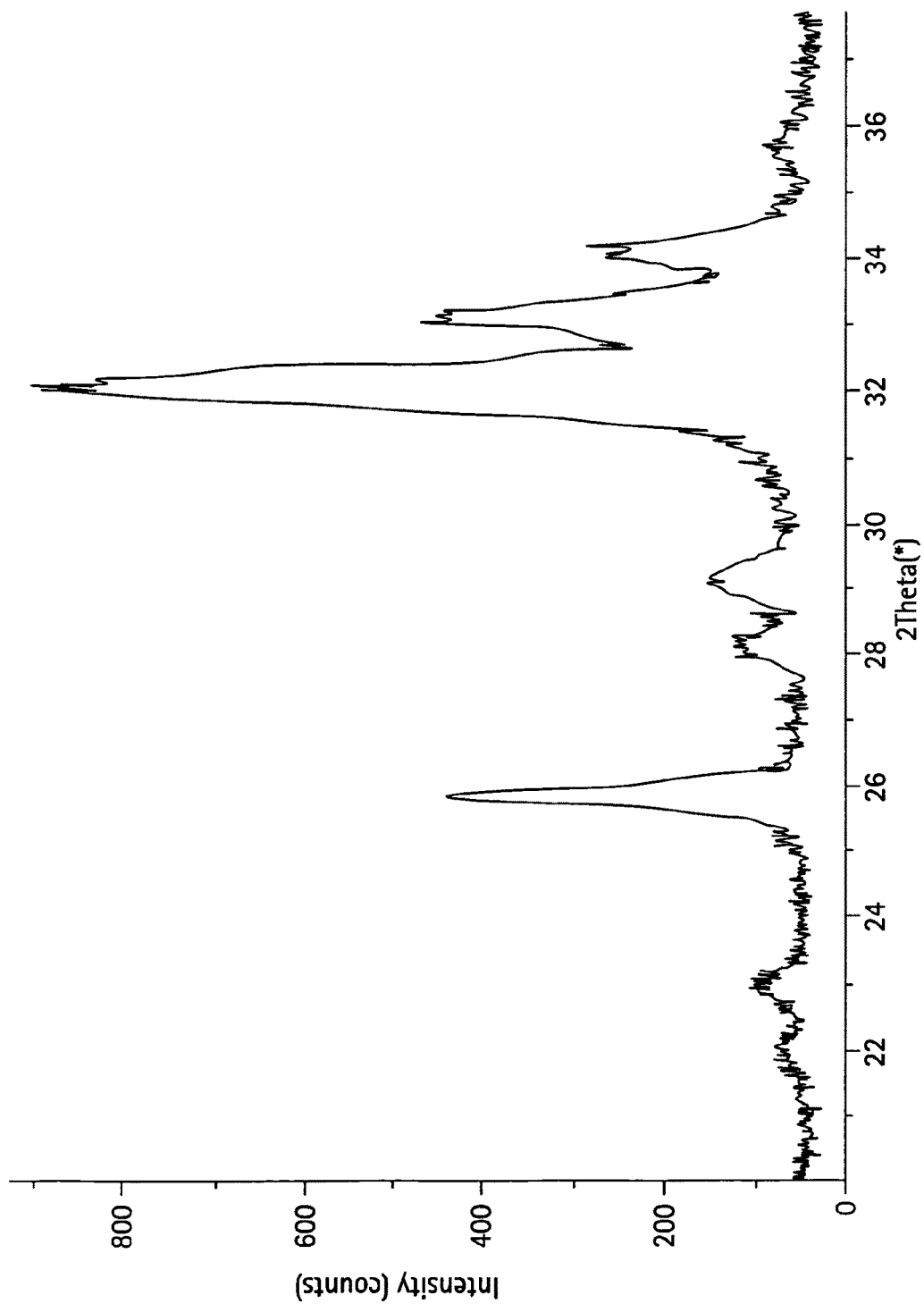

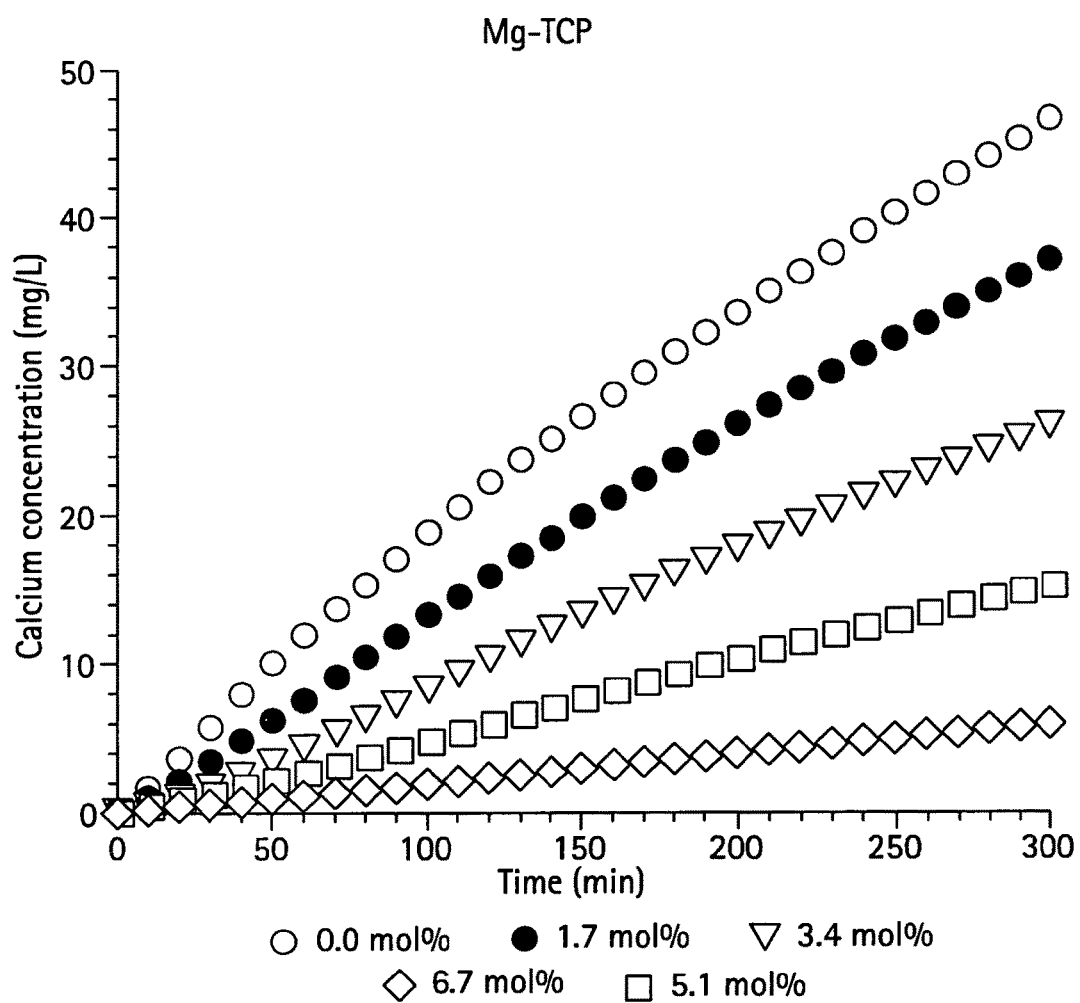

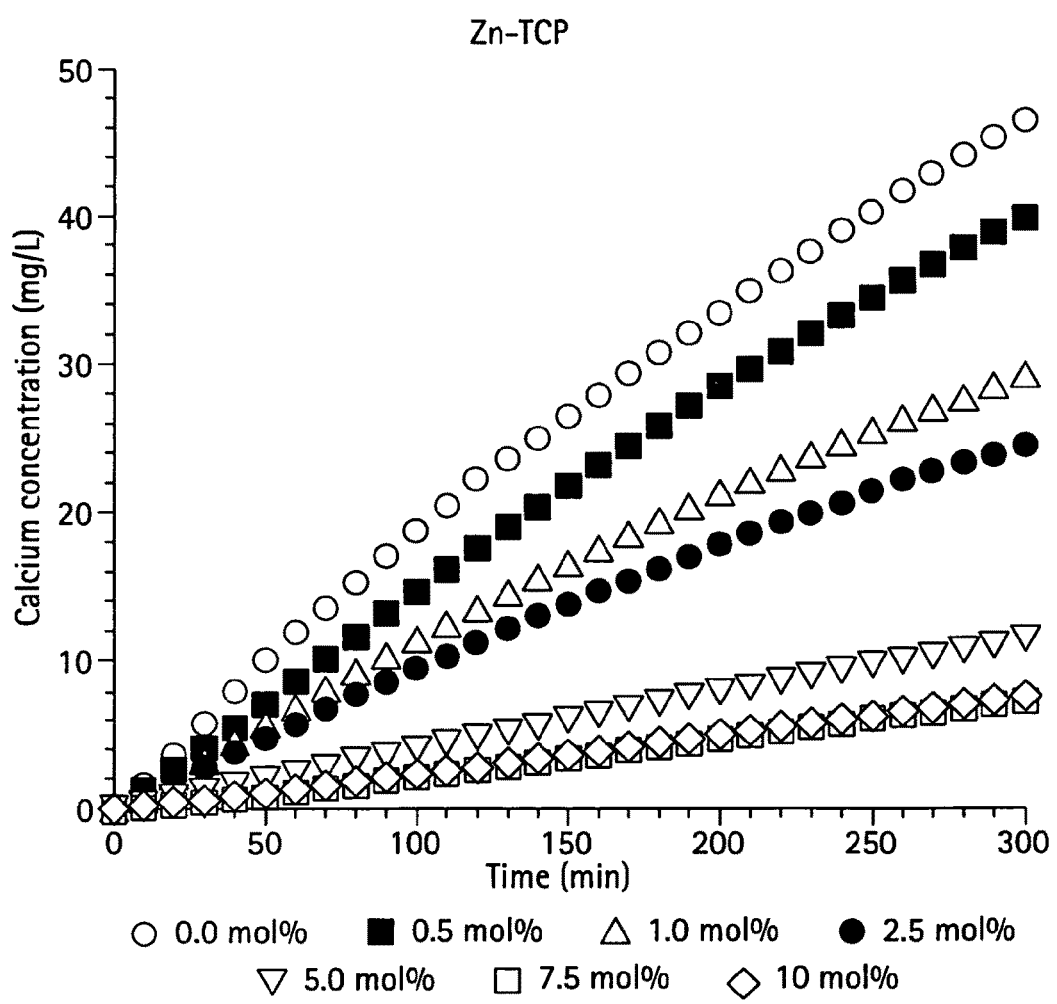

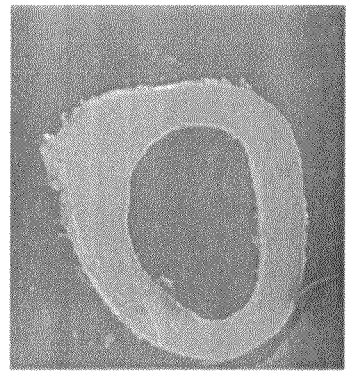
FIG. 12A
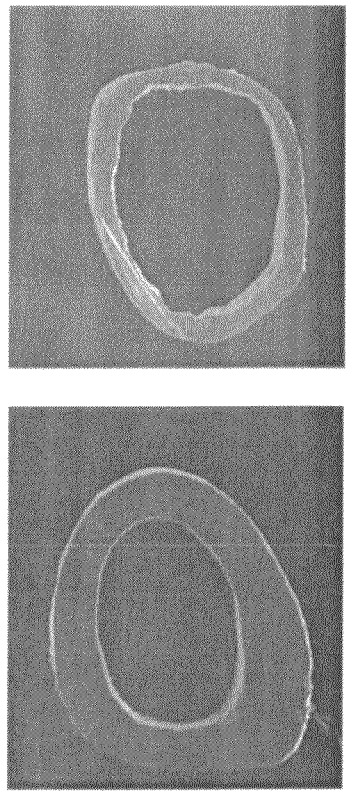
FIG. 12B
FIG. 12C
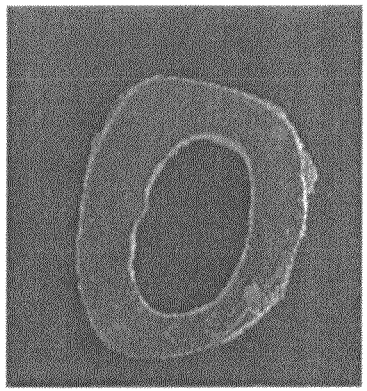
FIG. 12D
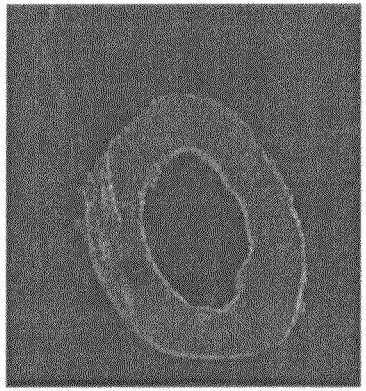
FIG. 12E
FIG. 12F

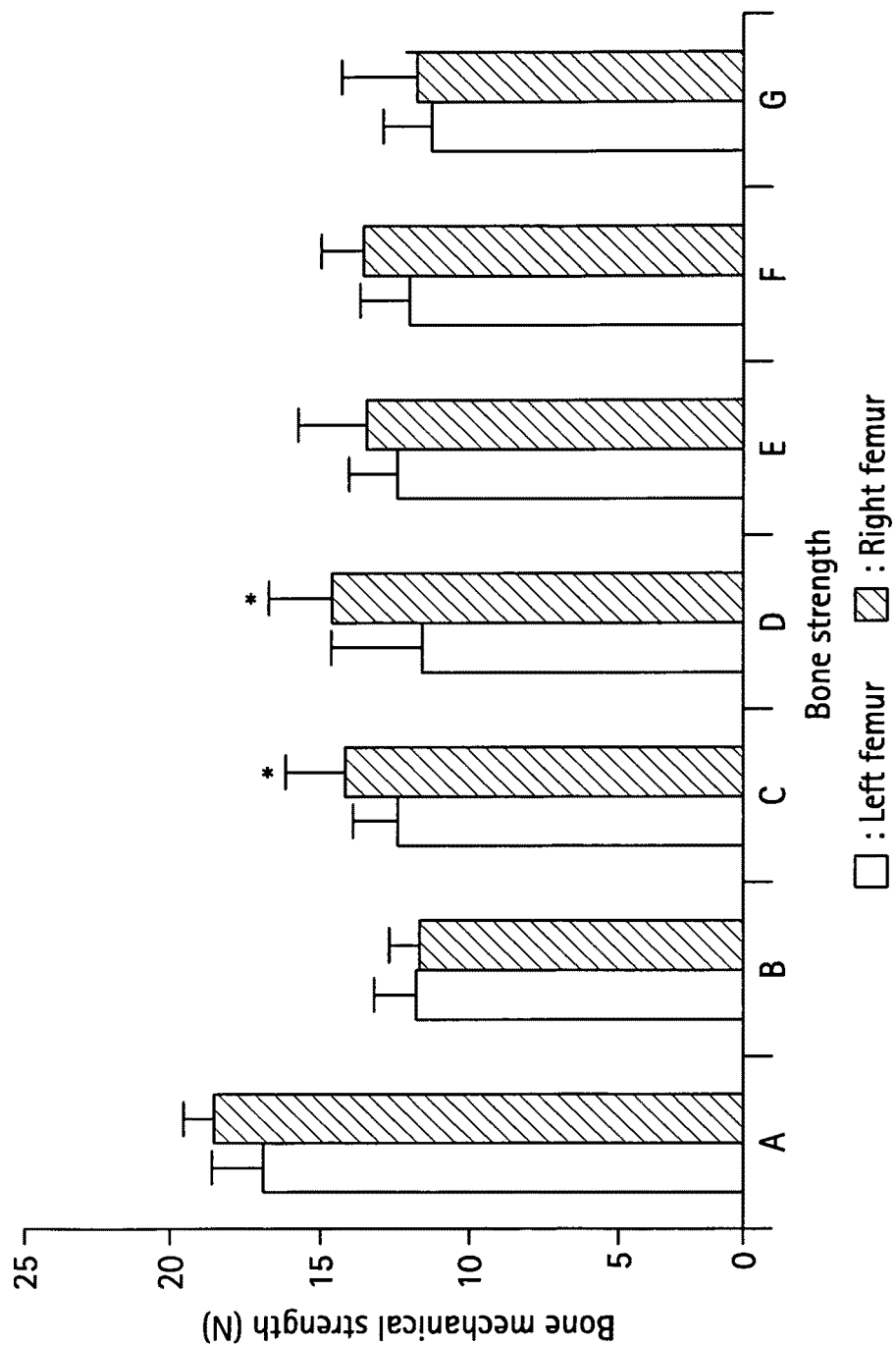

5.0 nm 5.0 nm

1 μm

1 μm

CALCIUM PHOSPHATE-BASED MATERIALS CONTAINING ZINC, MAGNESIUM, FLUORIDE AND CARBONATE

RELATED APPLICATIONS

This application is a continuation in part of U.S. Ser. No. 10/952,530, filed Sep. 28, 2004 now U.S. Pat. No. 7,419,680, which claims priority from U.S. Provisional Patent Application Ser. No. 60/507,593, filed Oct. 1, 2003.

FIELD OF THE INVENTION

This invention relates generally to compositions and methods useful in the prevention and treatment of osteoporosis and for bone and fracture repair. More specifically, the invention relates to slow-releasing calcium phosphate-based materials incorporating Mg, Zn, F, carbonate and optionally other ions such as, for instance, boron, strontium, manganese, copper, silicate, etc. or organic moieties such as, for instance, proteins, amino acids, nutraceuticals, etc. that may promote bone formation and inhibit bone resorption.

BACKGROUND OF THE INVENTION

Osteoporosis is a progressive and debilitating metabolic bone disease characterized by low bone mass (bone loss) and structural deterioration (thinning of the cortical bone and disorganization of the trabecular bone) leading to increased bone fragility and susceptibility to fractures especially of the hip (femoral head), spine (vertebrae) and the wrist. Osteoporosis is a 'silent' disease because related bone loss occurs without symptoms until the individual suffers a bone fracture. Worldwide, the number of hip fractures due to osteoporosis was projected to rise from 1.7 million in 1990 to 6.3 million by 2050. In the U.K., it was estimated that the National Health Service cost associated with osteoporosis is over L600 million ($1.02 billion) per year in 1991 and projected to increase considerably. In Japan, estimated number of hip fracture in 1998 was about 90,000/year with associated hospital cost of about $120 million per year. In the U.S., osteoporosis is responsible for more than 1.5 million fractures/year including: 300,000 hip fractures and approximately 700,000 vertebral fractures, 200,000 wrist fractures and 300,000 fractures in ribs and other sites. 12% to 20% of patients with hip fracture die within a year after the fracture, usually from complications related to either the fracture or surgery. In 2001, the estimated health care cost (hospitals and nursing homes) related to osteoporosis and associated fractures were $17 billion ($47 million/day!) and projected to increase to $30 to $40 billion annually in the next decade.

Bone tissue consists of two types: cortical (or compact bone) and trabecular (or spongy bone), differing in architecture, properties and function. The cortical bone provides mechanical strength and protective functions while cancellous or trabecular bone provides the metabolic functions. Two major processes are responsible for the development and maintenance of the bone tissue: bone formation (bone build-up) and bone resorption (bone modeling). During skeletal development in humans (birth to adulthood), the rate of bone formation is much greater than the rate of bone resorption until maximum bone mass (peak bone mass) is reached (at about age 35 for cortical bone and earlier for trabecular bone). After the peak bone mass is reached, the bone turnover per year is about 25% in trabecular bone and 3% in cortical bone. A bone remodeling process (bone turnover) in which the rates of bone formation and bone resorption are equal in the same site maintains the skeletal mass in adulthood. When these two processes are in equilibrium or are "coupled," there is no net gain or loss in bone mass. It is believed that the bone loss associated with primary type of osteoporosis results from the uncoupling of these two processes; with the rate of bone formation being much lower than the rate of resorption. A secondary type of osteoporosis is observed after prolonged immobilization and prolonged periods of bed rest or under glucocorticoid treatment for pulmonary disorders. In such conditions the mechanism of bone loss include both increased bone resorption and decreased bone formation. Reduction in bone formation leads to inadequate bone replacement during remodeling and to gradual bone loss resulting in the thinning of the cortical bone and reduction in cancellous bone formation.

Two major bone cells are involved—osteoblasts for bone formation and osteoclasts for bone resorption. Bone formation is reflected in osteoblast activities involving matrix (collagen, protein, DNA) formation and mineralization. Bone resorption is determined by the rate of osteoclast recruitment and the intensity of osteoclast activity manifested by the appearance of resorption pits. Most conditions leading to osteoporosis (including estrogen deficiency, hyperparathyroidism and hyperthyroidism) are associated with increased osteoclastic bone resorption and the inability of the bone formation process to keep up with the resorption process.

Bone is a composite of about 25 wt % biopolymer (organic matrix), 70 wt % mineral or inorganic phase, and 5 wt % water. The organic matrix is principally (about 95%) of Type I collagen with non-collageneous proteins. Osteoporosis is characterized by bone loss, decreased bone strength, lower bone density, poorer bone quality (e.g., porous cortical bone), thinning cortical bone and disorganized trabecular bone. Bone loss is often a predictor of future fracture risk.

In bone resorption, dissolution of the bone mineral occurs before the degradation of the collagen fibers. The rate of osteoclastic destruction of mineralized tissues was observed to be inversely proportional to bone mineral density. The bone mineral or inorganic component of bone is a calcium phosphate idealized as a calcium hydroxyapatite, $Ca_{10}(PO_4)_6(OH)_2$. However, comprehensive studies on synthetic and biologic apatites demonstrate convincingly that biologic apatites (mineral phases of enamel, dentin, cementum and bone) are apatites containing minor constituents (carbonate and magnesium) and are more accurately described as carbonate hydroxyapatite, approximated by the formula, $(Ca,Na,Mg)_{10}(PO_4,HPO_4,CO_3)_6(OH)_2$. Changes in the composition of the apatite affect its lattice parameters, morphology, crystallinity (reflecting crystal size and/or perfection) and dissolution properties. For example, Mg-for-Ca or $CO_3$-for-$PO_4$ substitution decreases crystallinity (crystal size) and increases solubility while F-for-OH substitution increases crystal size and decreases the solubility of synthetic apatites.

Osteoporotic bones were observed to have lower magnesium (Mg) and carbonate ($CO_3$) concentrations. Along with decreased Mg and $CO_3$ contents, larger bone apatite crystals (based on infrared spectroscopic measurements of 'crystallinity index') were reported in bones from patients with post-menopausal osteoporosis and alcoholic osteoporosis. Smaller bone apatite crystals were observed in bones of rats fed excess Mg while bone apatite crystals increased in size in bones from Mg-deficient rats. Enamel crystals of rats injected with Mg were smaller than those of the controls. On the other hand, bone apatite crystals from rats drinking high levels of fluoride (F) were larger and less soluble. Increase in width of bone apatite crystals were also observed in the bones of F-treated rabbits. Larger enamel apatite crystals in rat's teeth were observed after F administration.

Although there is still no known cure for osteoporosis, some medications have been approved by the FDA for postmenopausal women to prevent and/or treat osteoporosis. These include biphosphonates such as alendronate (Fosamax) and Risedmate (Actonel), Calcitonin (e.g., Miacalcin), estrogen (e.g., Climara, Estrace, Estraderm, Estratab, Ogen, Orto-Es, Viovlle, Premarin, etc) and hormones (estrogens and progestins (e.g., Activella, FemJHrt, Premphase, Prempro, etc); and selective estrogen receptor modulators, SERMs such as ralozifene (Evista). Sodium fluoride (NaF) treatment is pending approval. Treatments under investigation include parathyroid hormone (PTH), vitamin D metabolites, other biphosphonates, and SERMs. These therapeutic agents, except F therapy, are described as anti-resorptive agents because they principally target bone resorption. These therapeutic agents are associated with some serious side effects. For example, estrogen therapy is associated with cancer while bisphosphonate-based drugs are associated with osteonecrosis of the jaw and delayed healing.

Currently, experimental fluoride compounds recommended for osteoporosis therapy include sodium fluoride (NaF), monosodiumfluorophosphate, MFP, ($Na_2PO_3F$) and slow release preparation of NaF (SR—NaF). There is general agreement that F stimulates bone formation directly without the need for prior bone resorption and that it is this uncoupling of resorption and formation that makes this element so effective in increasing bone mass. However, fluoride therapy has also been associated with increased fracture risk despite increased bone mass.

The bone mineral can best be described as a carbonate hydroxyapatite, approximated by the formula: $(Ca,Na,Mg)_{10}(PO_4,CO_3,HPO_4)_6(OH,Cl)_2$ containing about 40% calcium. Calcium is stored in bone in the process of mineralizing newly deposited tissue and it is withdrawn from bone only by resorption of old bone tissue. The biological fluids are metastable with respect to apatite, maintaining the integrity of the bone and tooth mineral (apatite). Ca deficiency in the diet induces osteoporosis in rats. Ca supplementation is strongly recommended for optimum bone health. Ca supplementation has been reported to reduce cortical bone loss during the first 5 years of menopause and produce a sustained reduction in the rate of total body bone loss at least 3 years after menopause. However, by itself, Ca supplementation does not appear to slow the rapid loss of trabecular bone during the first few years of menopause nor does it prevent the menopause-related lumbar bone loss. A study on spinal bone loss in postmenopausal women supplemented with Ca and trace minerals (zinc, manganese and copper) showed that bone loss was arrested by intake of Ca plus trace minerals while no difference was observed between the placebo group or group receiving Ca alone.

Magnesium (Mg) is an important element in biological systems. 50% to 60% of Mg in the body is associated with the bone mineral. The rest of the Mg in the body is intracellular, a required co-factor in more than 300 enzyme systems. Mg is critical for cellular functions that include oxidative phosphorylation, glycolysis, DNA transcription and protein and nucleic acid synthesis. Mg deficient diet in rats was shown to have impaired bone growth (reduction in bone formation and bone volume), decreased bone strength and increased fragility. These and other animal studies implicate Mg deficient diet as a possible risk factor for osteoporosis. In humans, Mg deficiency in the diet was also associated with osteoporosis. Mg therapy was reported to increase bone mass in postmenopausal osteoporosis. Other studies suggest that Mg supplementation suppresses bone turnover rates in young adult males. On the cellular level, in vitro, an isolated report indicates that Mg directly stimulated osteoblast proliferation.

Zn is an essential trace element in the activity of more than 300 enzymes and affects basic processes of cell division, differentiation, and development and is required in collagen biosynthesis and in the biosynthesis and repair of DNA, in matrix and protein synthesis and plays an important role in bone metabolism and growth. It is the most abundant trace metal in bone mineral, being present at a concentration of up to 300 ppm. Zn deficiency in rats was shown to result in a 45% reduction in cancellous bone mass and to a deterioration of trabecular bone architecture, with fewer and thinner trabeculae and therefore may be considered as a risk factor in the development of osteoporosis. In vivo, Zn was shown to stimulate bone formation in weanling rats and in aged rats.

On the cellular level in vitro, Zn has been shown to have a stimulatory effect on bone formation and an inhibitory or biphasic effect on osteoclastic bone resorption. Studies on Zn-releasing compounds such as b-alanyl-L-histadanato zinc and Zn-TCP demonstrated that Zn promoted greater bone formation in vitro and was effective in increasing bone density or in preventing bone loss in vivo.

On the crystal level in synthetic systems, the presence of Zn causes the formation of apatite with low crystallinity, promoting the formation of Zn-substituted β-TCP or even amorphous calcium phosphate (ACP), depending on the solution Zn/Ca molar ratio. Both Mg and Zn were shown to inhibit the growth of apatite.

The relevant literature suggests that Mg or Zn separately may have beneficial effects on bone matrix but may cause the formation of bone apatite with low crystallnity (small crystal size). On the other hand, F may improve crystallinity (larger crystal size) and reduce solubility of bone apatite, but may cause impaired or abnormal mineralization. Separately, Mg, Zn and F ions have been associated with promotion of osteoblastic activity (bone formation) and/or inhibition of osteoclastic activity (bone resorption). Zn-releasing compounds, such as b-alanyl-l-histadano zinc compounds and Zn-TCP have been shown to have therapeutic effect on osteoporosis in rats induced by zinc-deficiency. Mg and Zn deficiencies have been reported as risk factors for osteoporosis. F compounds (NaF, monofluorophosphate and slow-releasing NaF) are used in the management of osteoporosis.

SUMMARY OF THE INVENTION

The present invention provides novel biomaterials comprising one or more of the following ions: magnesium (Mg), zinc (Zn) and fluoride (F) ions in a carbonate-containing apatite or biphasic calcium phosphate, BCP system. The present invention may consist of carbonate apatite and tricalcium phosphate incorporating Mg, Zn, F or other ions. In some embodiments, the biomaterial contains Mg, in some embodiments Zn, in some embodiments F, in some embodiments Mg and Zn, in some embodiments Mg and F, in some embodiments Zn and F, and in some embodiments Mg, Zn and F. In some embodiments, the biomaterial may contain one or more additional ions, for instance, strontium, boron, manganese, copper, silicate, etc. In yet other embodiments, the biomaterial may contain one or more additional compounds, such as, for instance, nutraceuticals that have anti-inflammatory, antibacterial or anti-oxidant properties or activity. In still further embodiments, the biomaterial may contain one or more additional protein or peptide. In preferred embodiments, the biomaterial is substantially free of serious side effects or deleterious effects on bone strength and fracture incidence such as those associated with the presently FDA-approved anti-resorptive agents. The biomaterial may be substantially similar in composition to bone mineral (a carbonate apatite). In some embodiments, the biomaterial features slow release of Mg, Zn, F, Ca, and P ions. In other embodiments, the biomaterial combines ions in preferred concentrations known separately to promote bone formation and minimize or prevent bone resorption. In yet other embodiments, the biomaterial allows the incorporation of lower levels of these ions thus avoiding deleterious effects observed with higher levels. In still other embodiments, the biomaterial provides beneficial effects of Mg and Zn on collagen and protein formation to balance the F effect on bone apatite formation and crystal size thereby promoting formation of bone with higher mineral density and greater bone mass. In yet other embodiments, the biomaterial provides synergistic effects of the three elements on bone resorption to allow the rate of bone formation to catch up with the rate of bone resorption, resulting in a net gain in bone mass. The biomaterials of the present invention may be useful for reducing the development of osteoporosis or even preventing osteoporosis, increasing cancellous bone mass and arresting the progress of osteoporosis, reversing bone loss and repairing fractures such as those caused by osteoporosis. The biomaterials may also be used in treating other bone deficiency caused by mineral deficiency or diseases such as cancer or osteopenia or therapies such as steroid treatments or radiation or conditions such as immobilization).

The biphasic calcium phosphate, BCP, may be, in one embodiment, a mixture of unsubstituted hydroxyapatite (HA) or substituted HA or substituted carbonate apatite and unsubstituted β-TCP, $Ca_3(PO_4)_2$ or substituted β-TCP. BCP of varying HA/-TCP ratios may be produced directly or by sintering calcium-deficient apatite, for instance having a Ca/P<1.67, that has been prepared either by a precipitation or by a hydrolysis method or by a solid-state reaction.

In some embodiments, the amount of each component (by weight %) present in the biomaterials of the invention may be as follows: Mg, 0.0.05 to 20 wt %, Zn, 0.02 to 20 wt %, F, 0.0 to 4 wt %, calcium (Ca commonly designated "C" herein as in "TCP" or "BCP") 10 to 50 wt %, phosphate (commonly designated "P" herein, as in "TCP" or "BCP") 5 to 30 wt %, carbonate ($CO_3$) 0.5 to 25 wt %. In other embodiments, the amount of each component (by weight %) present in the biomaterials of the invention may be as follows: Mg, 0.05 to 12 wt %; Zn, 0.02 to 12 wt %; F, 0.0 to 4 wt %, calcium (Ca commonly designated "C" herein as in "TCP" or "BCP"), 20 to 40 wt %; phosphate, (commonly designated "P" herein, as in "TCP" or "BCP") 10 to 20 wt %; carbonate ($CO_3$). 1 to 20 wt %. In some embodiments, the biomaterial contains Ca, P, and $CO_3$. The biomaterial may also be combined with one or more organic moieties such as proteins, amino acids, nutraceuticals with antibacterial, antioxidante and anti-inflammatory properties known to inhibit osteoclastic activity or promote osteoblastic activity. The biomaterial may be unsintered or sintered (heated) at temperatures of, for instance, about 200° to 1000° C. The biomaterial may be used as a diet supplement representing from about 0.01 to 5 wt. % of the total diet, or as bone-graft material or scaffold for tissue engineering. The biomaterial may be in any form including: powder, granule, block, in a carrier (e.g., a saline solution or a polymer solution) for injection at local sites, and may be in the form of an injectable cement.

In a second aspect, the invention provides methods of inhibiting bone resorption by administering a biomaterial comprising one or more of Mg, Zn and F ions in a carbonate-containing apatite or in a biphasic calcium phosphate (BCP) system. In some embodiments, the biomaterial contains Mg, in some embodiments Zn, in some embodiments F, in some embodiments Mg and Zn, in some embodiments Mg and F, in some embodiments Zn and F, and in some embodiments Mg, Zn and F. In some embodiments, the biomaterial may contain one or more additional ions, for instance, strontium, boron, manganese, copper, silicate, etc. In yet other embodiments, the biomaterial may contain one or more additional compounds such as, for instance, nutraceuticals that have anti-oxidant, anti-inflammatory or antibacterial properties or activity. In still further embodiments, the biomaterial may contain one or more additional proteins or peptides. The biomaterial may be substantially similar in composition to bone mineral (a carbonate apatite). In some embodiments, the biomaterial features slow release of Mg, Zn, F, Ca, and P ions. The biphasic calcium phosphate, BCP, may be, in one embodiment, a mixture of unsubstituted hydroxyapatite (HA) or substituted HA or substituted carbonate apatite and unsubstituted β-TCP, $Ca_3(PO_4)_2$ or substituted β-TCP. BCP of varying HA/-TCP ratios may be produced directly or by sintering calcium-deficient apatite, for instance having a Ca/P<1.5, 1.6, 1.67, 1.75 or 1.8 that has been prepared either by a precipitation or by a hydrolysis method or by a solid-state reaction. In some embodiments, the amount of each component (by weight %) present in the biomaterials of the invention may be as follows: Mg 0.5 to 12 wt %, Zn 1 to 12 wt %, F 0.1 to 4 wt %, calcium (Ca commonly designated "C" herein as in "TCP" or "BCP") 20 to 40 wt %, phosphate (commonly designated "P" herein, as in "TCP" or "BCP") 10 to 20 wt %, carbonate ($CO_3$) 1 to 20 wt %. In some embodiments, the biomaterial contains Ca, P, and $CO_3$. The biomaterial may also be combined with one or more organic moieties such as moieties known to inhibit osteoclast activity. The biomaterial may be unsintered or sintered at 100 to 1000° C. The biomaterial may be used as a diet supplement or as bone-graft material or scaffold for tissue engineering. The biomaterial may be in any form including: powder, granule, a block, in a carrier (e.g., a saline solution or a polymer solution) for injection at local sites, and may be in the form of an injectable cement.

In a third aspect, the invention provides methods of treating osteoporosis or delaying the onset of osteoporosis by administering a biomaterial comprising one or more of Mg, Zn and F ions in a carbonate-containing apatite or biphasic calcium phosphate (BCP) system consisting of carbonate apatite and substituted β-TCP. In some embodiments, the biomaterial contains Mg, in some embodiments Zn, in some embodiments F, in some embodiments Mg and Zn, in some embodiments Mg and F, in some embodiments Zn and F, and in some embodiments Mg, Zn and F. The biomaterial may be substantially similar in composition to bone mineral (a carbonate apatite). In some embodiments, the biomaterial may contain one or more additional ions, for instance, strontium, boron, manganese, copper, silicate etc. In yet other embodiments, the biomaterial may contain one or more additional compounds that have anti-oxidant, anti-inflammatory, antibacterial, anti-oxidant properties or activity such as, for instance, a nutraceutical. In still further embodiments, the biomaterial may contain one or more additional protein or peptide. In some embodiments, the biomaterial features slow release of Mg, Zn, F, Ca, and P ions. The biphasic calcium phosphate, BCP, may be, in one embodiment, a mixture of unsubstituted hydroxyapatite (HA) or substituted HA or substituted carbonate apatite and unsubstituted β-TCP, $Ca_3(PO_4)_2$ or substituted β-TCP. BCP of varying HA/-TCP ratios may be produced directly or by sintering calcium-deficient apatite, for instance having a Ca/P<1.5, 1.6, 1.67, 1.75 or 1.8 that has been prepared either by a precipitation or by a hydrolysis method or by a solid-state reaction. In some embodiments, the amount of each component (by weight %) present in the biomaterials of the invention may be as follows: Mg 0.5 to 12 wt %, Zn 1 to 12 wt %, F 0.1 to 4 wt %, calcium (Ca commonly designated "C" herein as in "TCP" or "BCP") 20 to 40 wt %, phosphate (commonly designated "P" herein, as in "TCP" or "BCP") 10 to 20 wt %, carbonate ($CO_3$) 1 to 20 wt %. In some embodiments, the biomaterial contains Ca, P, and $CO_3$. The biomaterial may also be combined with one or more organic moieties such as moieties known to inhibit osteoclastic activity or promote osteoblastic activity. The biomaterial may be unsintered or sintered (heated) at temperatures of from about 100° to 1000° C. The biomaterial may be used as a diet supplement or as bone-graft material or scaffold for tissue engineering. The biomaterial may be in any form including a powder, granule, a block, in a carrier (e.g., a saline solution or a polymer solution) for injection at local sites, and may be in the form of an injectable cement.

In a fourth aspect, the invention provides methods of treating a bone fracture by administering a biomaterial comprising one or more of Mg, Zn and F ions in a carbonate-containing apatite or in a biphasic calcium phosphate (BCP) system. In some embodiments, the biomaterial contains Mg, in some embodiments Zn, in some embodiments F, in some embodiments Mg and Zn, in some embodiments Mg and F, in some embodiments Zn and F, and in some embodiments Mg, Zn and F. In some embodiments, the biomaterial may contain one or more additional ions, for instance, strontium, boron, manganese, etc. In yet other embodiments, the biomaterial may contain one or more additional compounds that have antioxidant properties or activity. In still further embodiments, the biomaterial may contain one or more additional protein or peptide. The biomaterial may be substantially similar in composition to bone mineral (a carbonate apatite). In some embodiments, the biomaterial features slow release of Mg, Zn, F, Ca, and P ions. The biphasic calcium phosphate, BCP, may be, in one embodiment, a mixture of unsubstituted hydroxyapatite (HA) or substituted HA or substituted carbonate apatite and unsubstituted and substituted β-TCP, $Ca_3(PO_4)_2$. BCP of varying HA/β-TCP ratios may be produced directly or by sintering calcium-deficient apatite, for instance having a Ca/P<1.5, 1.6, 1.67, 1.75 or 1.8 that has been prepared either by a precipitation or by a hydrolysis method or by a solid-state reaction. In some embodiments, the amount of each component (by weight %) present in the biomaterials of the invention may be as follows: Mg, 0.05 to 12 wt %; Zn, 0.01 to 12 wt %; F, 0.0 to 4 wt %; calcium (Ca commonly designated "C" herein as in "TCP" or "BCP"), 20 to 40 wt %; phosphate (commonly designated "P" herein, as in "TCP" or "BCP"), 10 to 20 wt %; carbonate ($CO_3$), 1 to 20 wt %. In some embodiments, the biomaterial contains Ca, P, and $CO_3$. The biomaterial may also be combined with one or more organic moieties such as proteins, peptides or nutraceuticals with antibacterial, antioxidant, anti-inflammatory properties known to inhibit osteoclastic activity or promote osteoblastic activity. The biomaterial may be unsintered or sintered (heated) at temperatures from about 100° to 1000° C. The biomaterial may be used as a diet supplement or as bone-graft material or scaffold for tissue engineering. The biomaterial may be in any form including a powder, granule, a block, in a carrier (e.g., a saline solution or a polymer solution) for injection at local sites, and may be in the form of an injectable cement.

In a fifth aspect, the invention provides methods of inhibiting osteoclast activity by administering a biomaterial comprising one or more of Mg, Zn and F ions in a carbonate-containing apatite or in a biphasic calcium phosphate (BCP) system consisting of carbonate apatite and substituted β-TCP. In some embodiments, the biomaterial contains Mg, in some embodiments Zn, in some embodiments F, in some embodiments Mg and Zn, in some embodiments Mg and F, in some embodiments Zn and F, and in some embodiments Mg, Zn and F. In some embodiments, the biomaterial may contain one or more additional ions, for instance, strontium, boron, manganese, copper, silicate, etc. In yet other embodiments, the biomaterial may contain one or more additional compounds such as, for example a neutraceutical that may have antioxidant, anti-inflammatory or antibacterial properties. In still further embodiments, the biomaterial may contain one or more additional protein or peptide. The biomaterial may be substantially similar in composition to bone mineral (a carbonate apatite). In some embodiments, the biomaterial features slow release of Mg, Zn, F, Ca, and P ions. The biphasic calcium phosphate, BCP, may be, in one embodiment, a mixture of unsubstituted hydroxyapatite (HA) or substituted HA or substituted carbonate apatite and unsubstituted and substituted β-TCP, $Ca_3(PO_4)_2$. BCP of varying HA/β-TCP ratios may be produced directly or by sintering calcium-deficient apatite, for instance having a Ca/P<1.5, 1.6, 1.67, 1.75 or 1.8 that has been prepared either by a precipitation or by a hydrolysis method or by a solid-state reaction. In some embodiments, the amount of each component (by weight %) present in the biomaterials of the invention may be as follows: Mg 0.5 to 12 wt %, Zn 1 to 12 wt %, F 0.1 to 4 wt %, calcium (Ca commonly designated "C" herein as in "TCP" or "BCP") 20 to 40 wt %, phosphate (commonly designated "P" herein, as in "TCP" or "BCP") 10 to 20 wt %, carbonate ($CO_3$) 1 to 20 wt %. In some embodiments, the biomaterial contains Ca, P, and $CO_3$. The biomaterial may also be combined with one or more organic moieties such as moieties known to inhibit osteoclastic activity and promote osteoblastic activity. The biomaterial may be unsintered or sintered (heated) at 100 to 1000° C. The biomaterial may be used as a diet supplement or as bone-graft material or scaffold for tissue engineering. The biomaterial may be in any form including a powder, granule, a block, in a carrier (e.g., a saline solution or a polymer solution) for injection at local sites, and may in the form of an injectable cement.

BRIEF DESCRIPTION OF DRAWINGS

FIG. 12 shows SEM images of cortical bone from rat on: (12A) normal diet; (12B) mineral deficient (MD) diet; (12C, 12D, 12E, 12F) MD supplemented with Mg—CaP, Zn—CaP, F—CaP and MZF-CaP, respectively. The cortical bone loss induced by MD diet (10B vs 10A) was prevented by the supplemented diets (12C, 12D, 12E, 12F compared to 12B).

DESCRIPTION OF PREFERRED EMBODIMENTS

The rationale for incorporating Mg, Zn and F in a carbonate apatite matrix was to combine these ions that had been separately associated with biomineralization in a matrix that is similar to bone mineral. Bone mineral is a carbonate apatite. (LeGeros R Z (1981) *Prog Crystal Growth Charact* 4:145).

Preparation of MZF-CaPs. Mg/F—CaP, Zn/F—CaP, Mg/Zn/F—CaP were prepared by a hydrolysis method at 90° C. from solutions with known Mg/Ca, Zn/Ca, $CO_3$/P and F/P molar ratios. X-ray diffraction (XRD) analysis confirmed earlier observations on the effect of Mg or Zn on the crystallinity of the apatite (FIG. 1), i.e., Mg or Zn tends to lower the crystallinity of apatite. Sintering at 600° C. increased the crystallinity (crystal size). When the concentration of either Mg or Zn in the CaP is higher than 5 wt %, sintering at 800° C., resulted in the formation of biphasic calcium phosphate, BCP, consisting of a mixture of apatite and Mg- and/or Zn-substituted β-TCP (FIG. 2C).

Composition of MZF-CaPs.

Elemental analyses using inductive coupled plasma (ICP) showed that the amount of Mg, Zn or F incorporated in the precipitated apatite depended on the solution concentrations of these ions (Table 1). The crystallinity, composition (Table 1, FIG. 8) and dissolution rates (release of ions) of the Mg/Zn/F—CaPs can be adjusted by manipulation of reaction condition, ion concentrations and sintering temperatures.

TABLE 1

Composition (wt %) and of MX + ZF—CaP preparations tested in animals

| Prep# | Ca | P | Mg | Zn | F | CO₃ | Ca/P | Mg/Ca | Zn/Ca | F/P | C/P | XRD* |
|---|---|---|---|---|---|---|---|---|---|---|---|---|
| #51 | 27.71 | 16.44 | 1.10 | 2.90 | 1.10 | 3.24 | 1.30 | 0.08 | 0.06 | 0.11 | 0.10 | AP |
| #52 | 27.57 | 15.73 | 0.18 | 0.01 | 1.21 | 4.32 | 1.38 | 0.01 | 0.00 | 0.13 | 0.14 | AP |
| #53 | 26.75 | 17.74 | 4.10 | 0.01 | 0.05 | 4.41 | 1.17 | 0.25 | 0.00 | 0.00 | 0.13 | AP |
| #54 | 21.94 | 14.71 | 0.16 | 8.40 | 0.05 | 5.48 | 1.17 | 0.01 | 0.19 | 0.00 | 0.19 | BCP |
| #68 | 27.71 | 16.44 | 2.70 | 2.85 | 2.31 | 3.62 | 1.30 | 0.17 | 0.06 | 0.03 | 0.12 | AP |
| #74 | 27.19 | 16.76 | 2.00 | 2.24 | 1.50 | 3.60 | 1.26 | 0.12 | 0.09 | 0.15 | 0.11 | AP |
| #76 | 28.54 | 15.98 | 1.95 | 2.44 | 3.00 | 2.39 | 1.38 | 0.11 | 0.05 | 0.31 | 0.08 | AP |
| #86 | 22.19 | 13.64 | 2.26 | 2.23 | 1.00 | 3.69 | 1.25 | 0.17 | 0.06 | 0.12 | 0.14 | AP |

*XRD: AP, apatite; BCP, biphasic calcium phosphate (mixture of Xn-substituted tricalcium phosphate and AP Dissolution Properties of MZF-CaPs.

Figure 3:
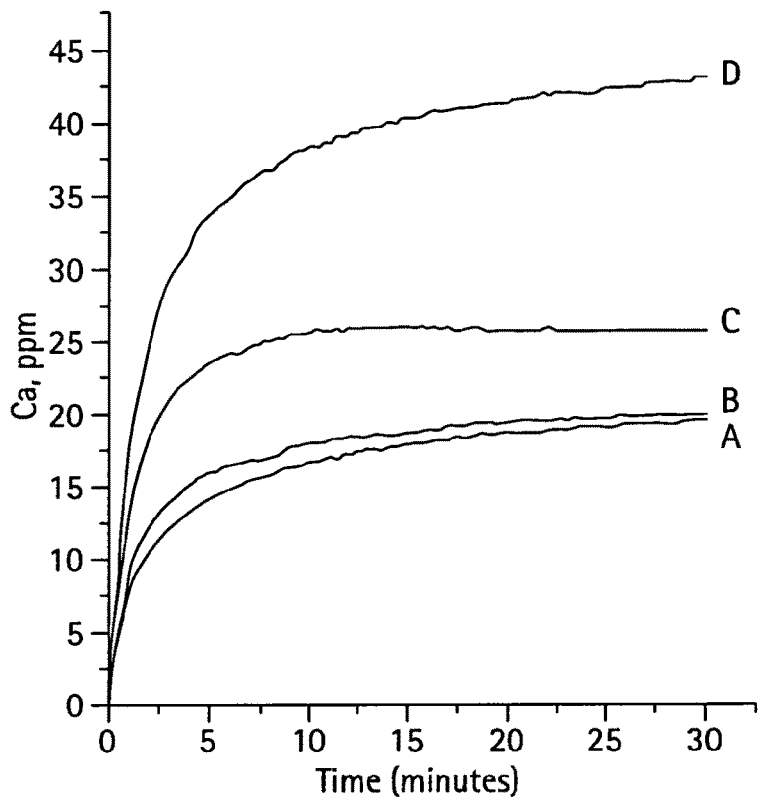
FIG. 3 shows dissolution reflected by the release of $Ca^{2+}$ ions with time from the synthetic calcium phosphates: (A) F—CaP; (B) Zn/F—CaP; (C) Mg/F—CaP and (D) Mg/Zn/F—CaP.
Figure 4:
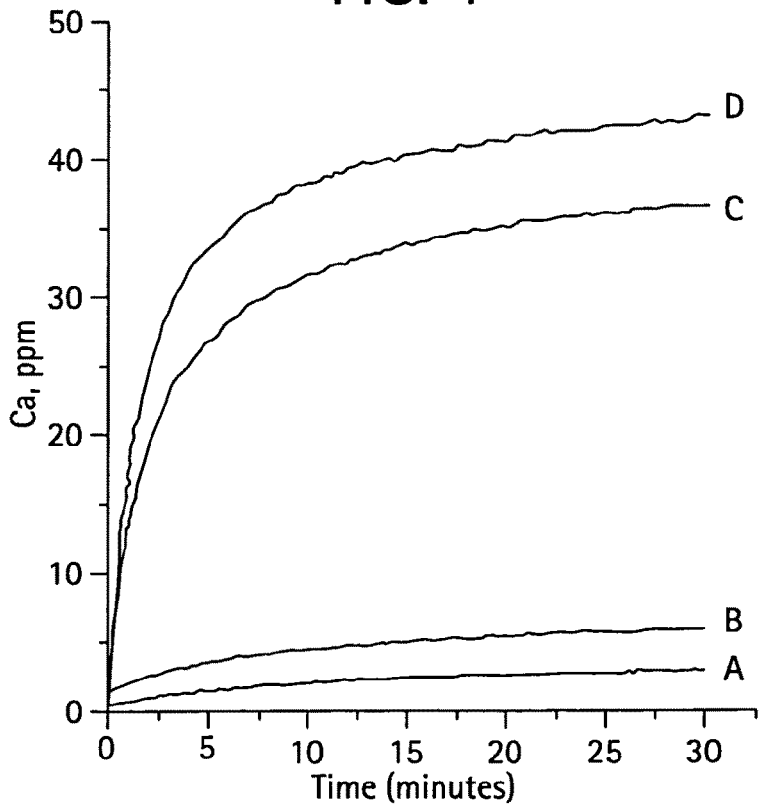
FIG. 4 shows dissolution reflected by release of $Ca^{2+}$ ions with time of Mg/Zn/F—CaP: before (C, D) and after ignition at 600° C. (B) and at 800° C. (A). C and D have similar concentrations of Mg and Zn but different concentrations of F, with (D) having the lower F concentration. The initial dissolution rate is decreased with increasing sintering temperature (A and B vs. C and D) and with increasing F concentration (A vs. B, C vs. D).

It has been demonstrated that an acidic microenvironment is fundamental to the resorptive process by the osteoclasts. Therefore, in vitro dissolution properties of the Mg/Zn/F-BCP materials under acidic conditions is predictive of in vivo degradation of these materials. For example β-TCP shown to be more soluble than HA in vitro and was also shown to have greater degradation in vivo. The rate of release of the essential elements (Mg, Zn and F) obtained in vitro gives an insight into their rate of release in vivo. Incorporation of Mg or Zn increased while incorporation of F decreased extent of dissolution of MZF-CaPs as measured by the Ca release (FIG. 3). The extent of dissolution decreased with increasing sintering temperature and with increasing amount of F (FIG. 4). Maximum release was observed after 10-minute exposure in the acidic buffer (0.1M NaAc, pH 5, 37° C.).

Results from the in vitro dissolution study of experimental synthetic materials provides information on the rate of release of Mg, Zn, F, Ca and P from the Mg/Zn/F—CaP materials and give insight into their release and availability in vivo. The dissolution is affected by the following factors: composition (the greater the F content, the lower the dissolution rate); sintering temperature (sintered materials have a slower rate of dissolution than uncalcined or unsintered materials), particle size, porosity and surface area and possibly physical form (e.g., powder vs. discs). The slow release of these ions from the Mg/Zn/F-BCP materials avoids the side effects observed for the fast releasing materials such as those reported for NaF.

Effect of MZF-CaPs on Bone Cell Activities.

Bones are constantly being remodeled throughout life. Under normal conditions, bones are being dissolved by osteoclasts and rebuilt by osteoblasts under exquisite regulatory control. In pathologic conditions such as osteoporosis, the tightly controlled bone remodeling process is disrupted and osteoclast activity outpaces bone production by osteoblasts. Laboratory models that can characterize the behavior of osteoclasts and osteoblasts at the cellular and molecular level provide critical insights into the pathophysiology of bone remodeling. In vitro cell models are important tools that address this problem. Osteoblast-like cells that exhibit characteristics of normal osteoblasts including synthesis of bone matrix component: collagen type I, osteocalcin, osteopontin and osteonectin help evaluate the effects of Mg/Zn/F-BCPs on cellular events involved in bone formation. Similarly, osteoclast-like cells derived from the bone marrow help clarify the effect of Mg/Zn/F-BCPs on bone resorption. In vitro cell models have also been instrumental in screening various agents and biomaterials for clinical application in a cost-effective way.

Figure 5:
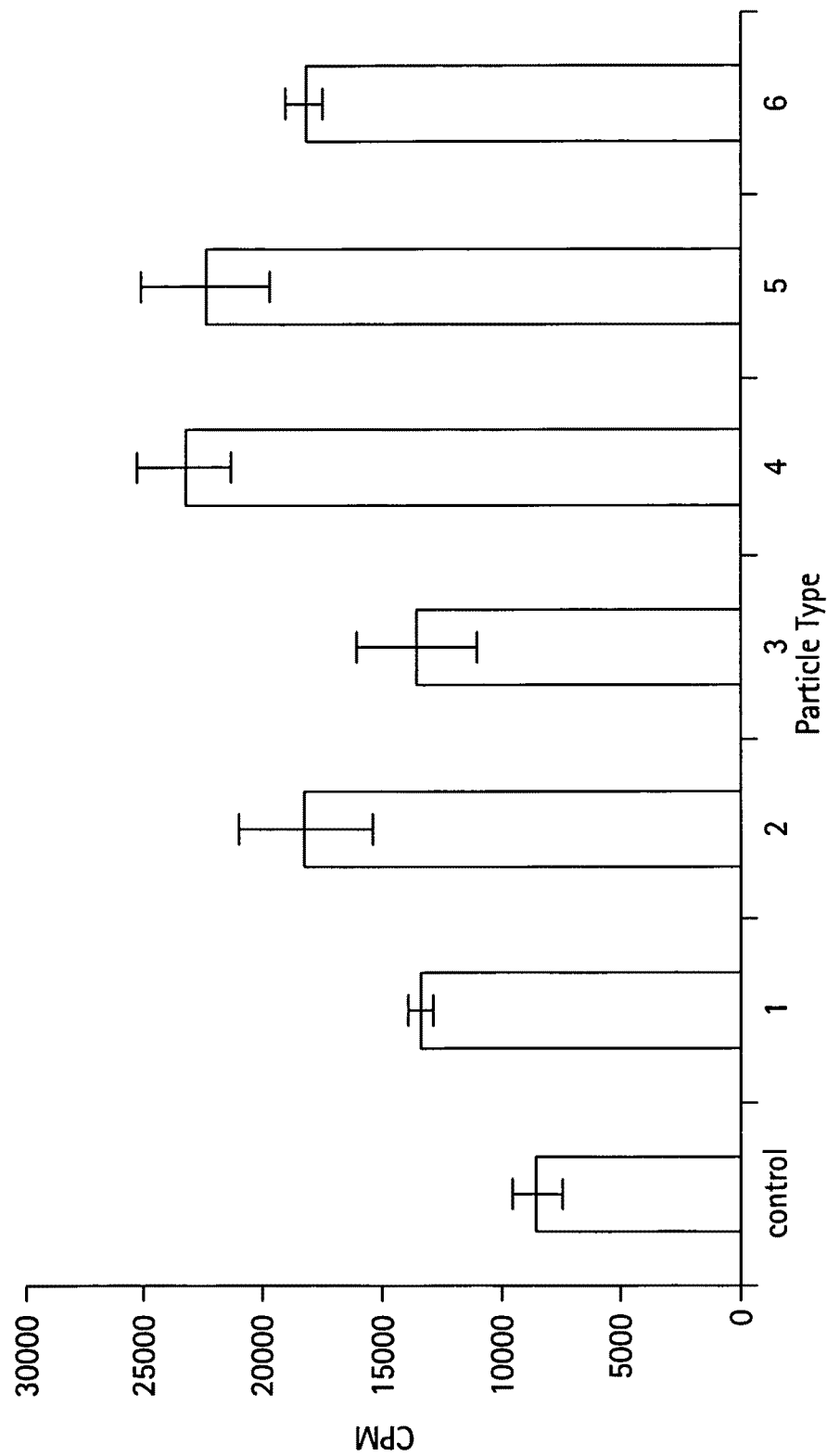
FIG. 5 shows the enhancing effect of MZF-CaPs on the proliferation of human osteoblast-like cells (MG-63) compared to control.
Figure 6:
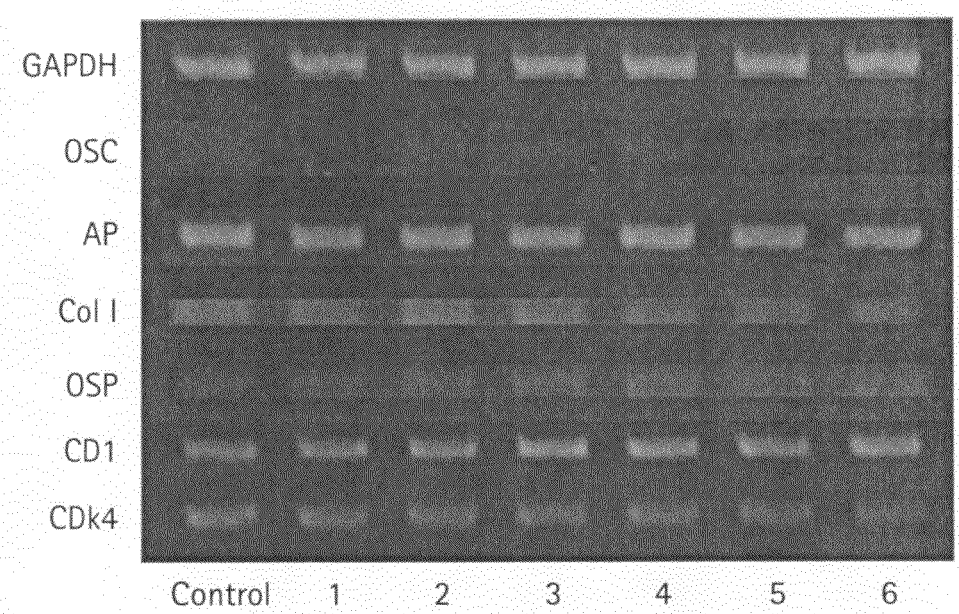
FIG. 6 shows the effect of MZF-CaPs on the phenotype expression of bone growth markers by the osteoblast-like cells (MG-63). Bone markers expressed are: osteocalcin (OSC), alkaline phosphatase (AP), collagen type 1 (Col 1), osteopontin (OSP).
Figure 7:
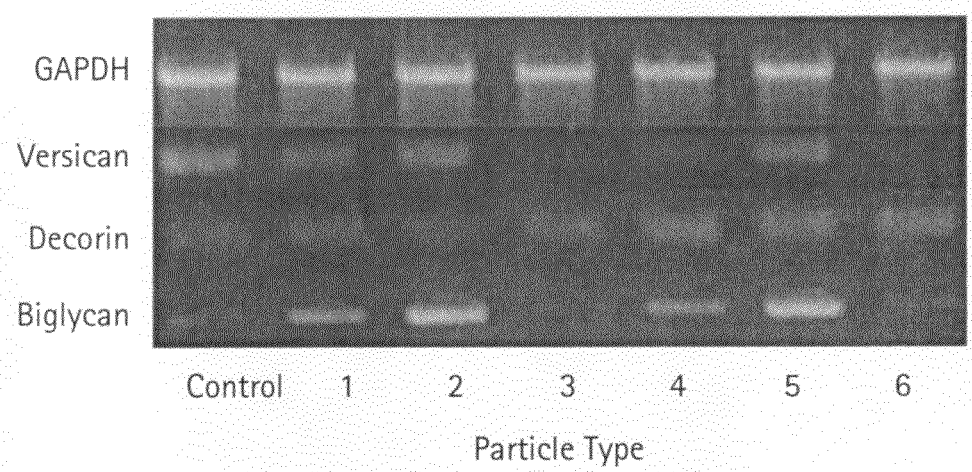
FIG. 7 shows the effect of BCPs on expression of proteoglycans (versican, deconsin, biglycan) by human osteoblast cells.
Figure 8B:
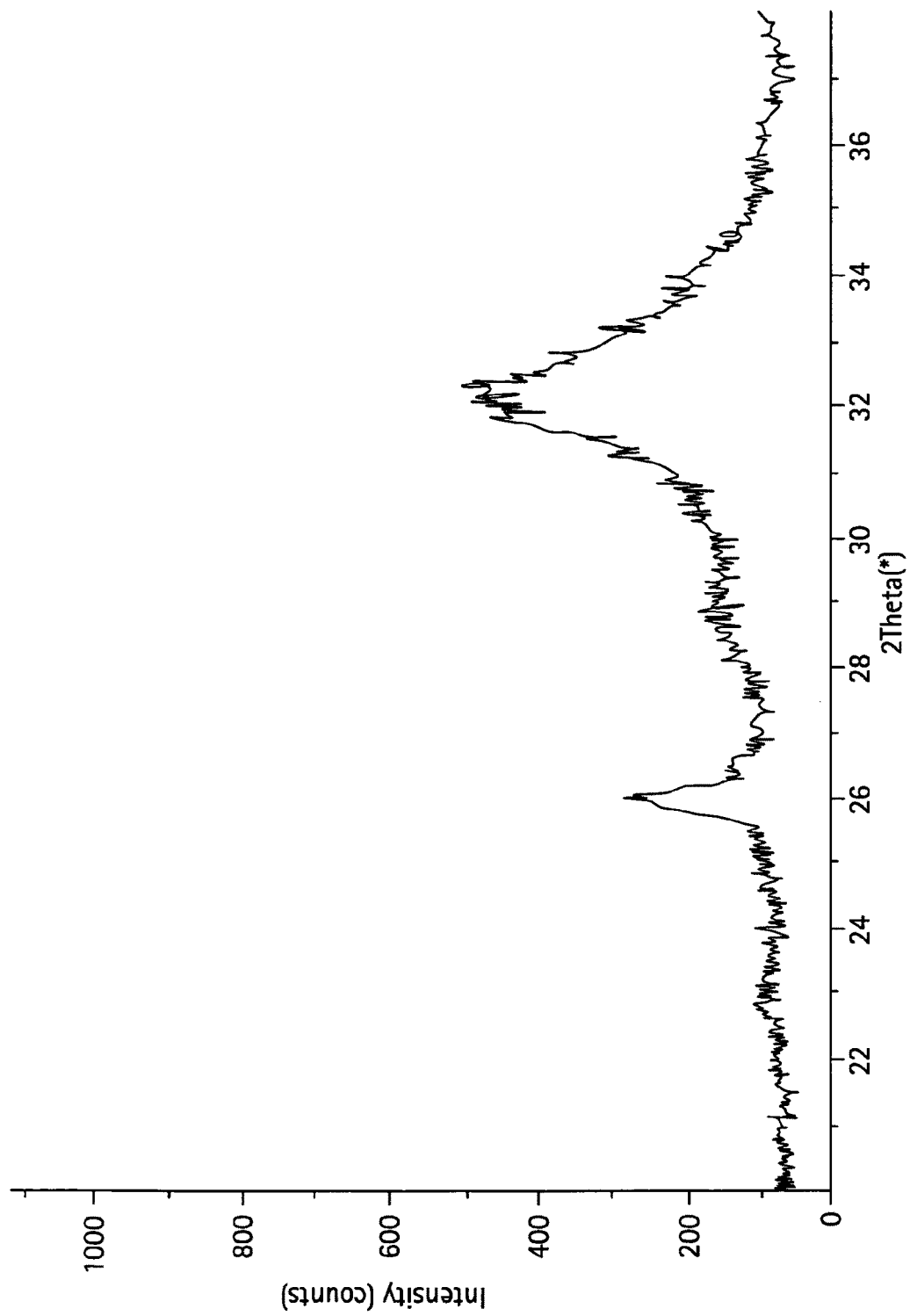
FIG. 8 shows XRD profiles (A,B,C,D) and FT-IR spectra (E). XRD profiles: (A) F—CaP; (B) Mg—CaP; (C) Zn—CaP; (D1,D2) MZF-CaPs compared to that of (D3) bone. When Mg or Zn concentrations in the CaP is higher than 5 wt %, two phases are observed: apatite and Mg- or Zn-TCP (C). FT-IR spectra: (EC, EB) MZF-CaPs compared to that of rat bone (EA), showing that the matrix of MZF-CaPs (EC, EB) is a carbonate apatite similar to bone (EA).
Figure 8C:
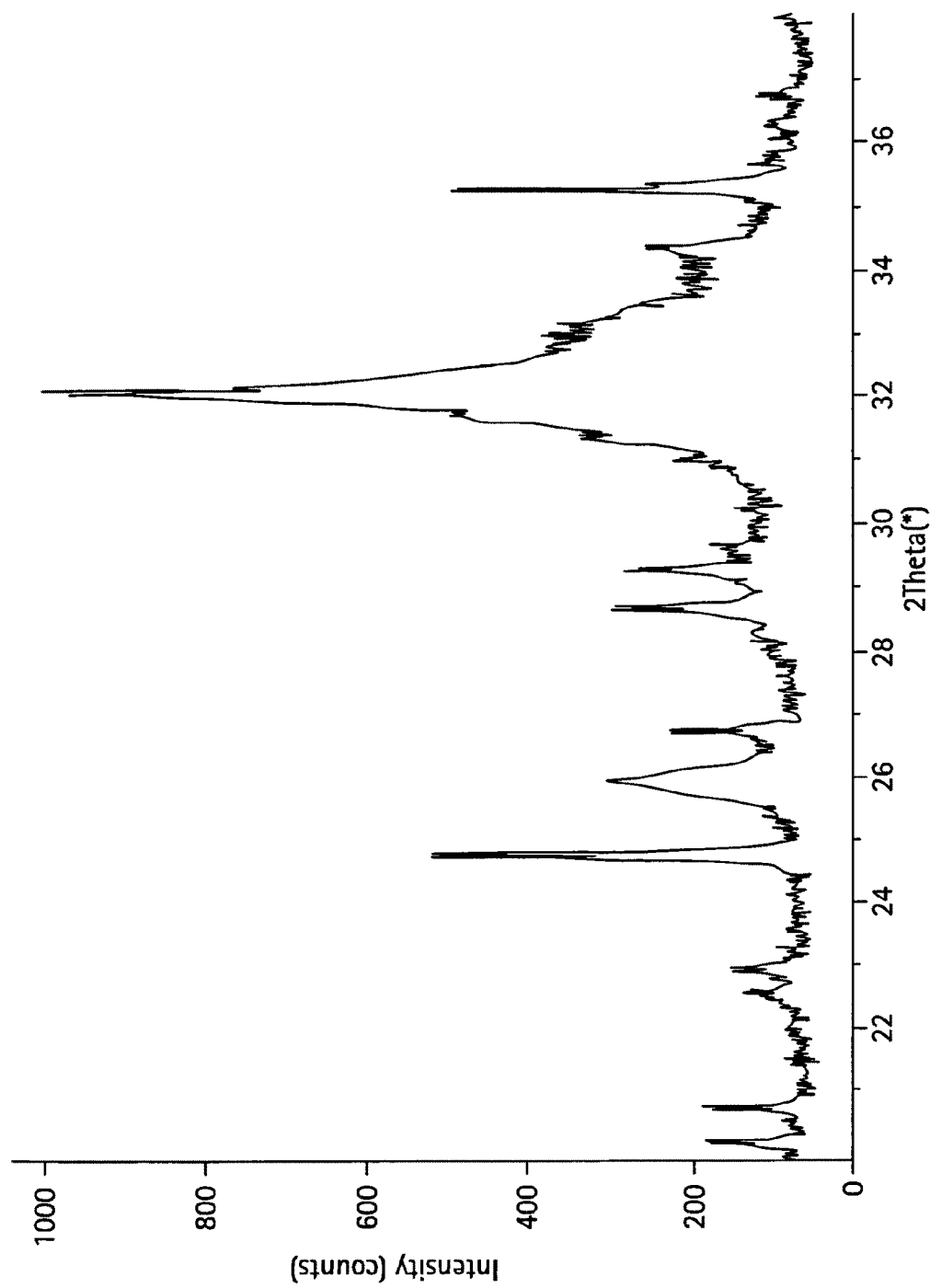
Figure 8D:
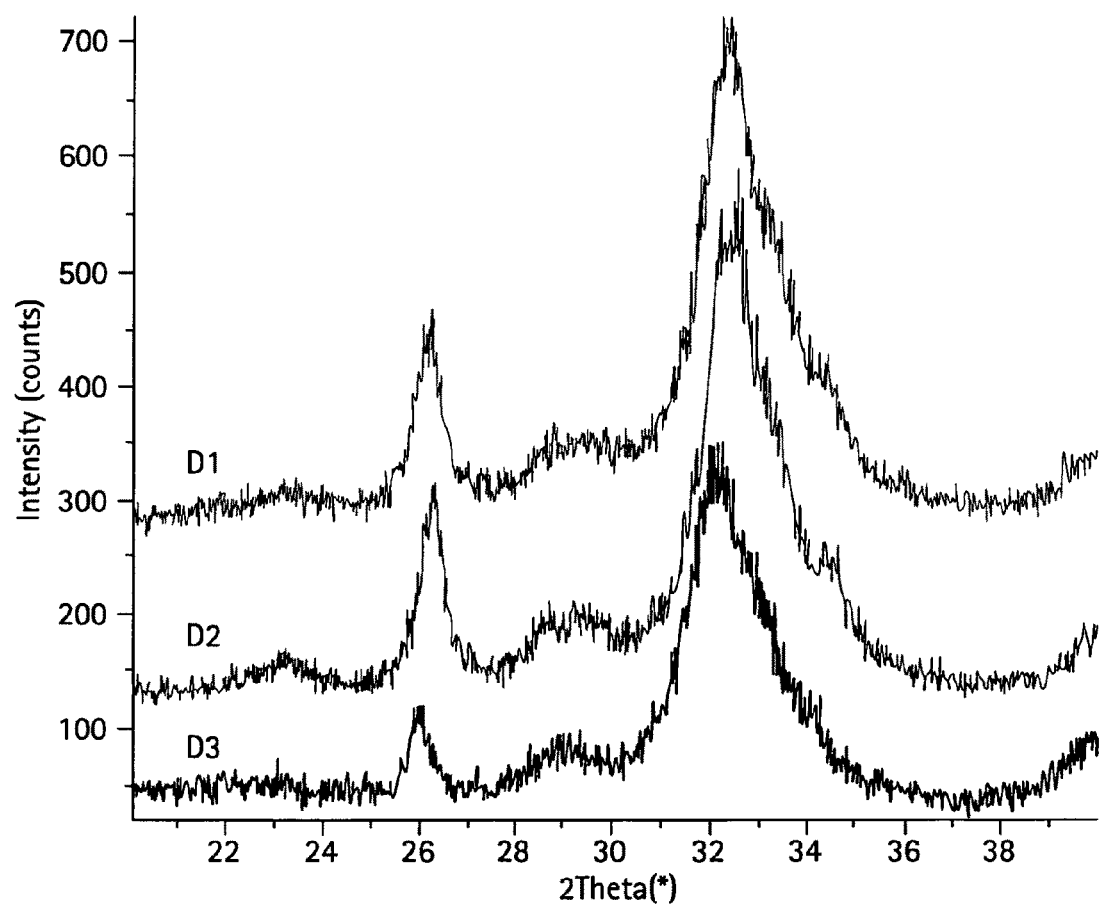
Figure 8E:
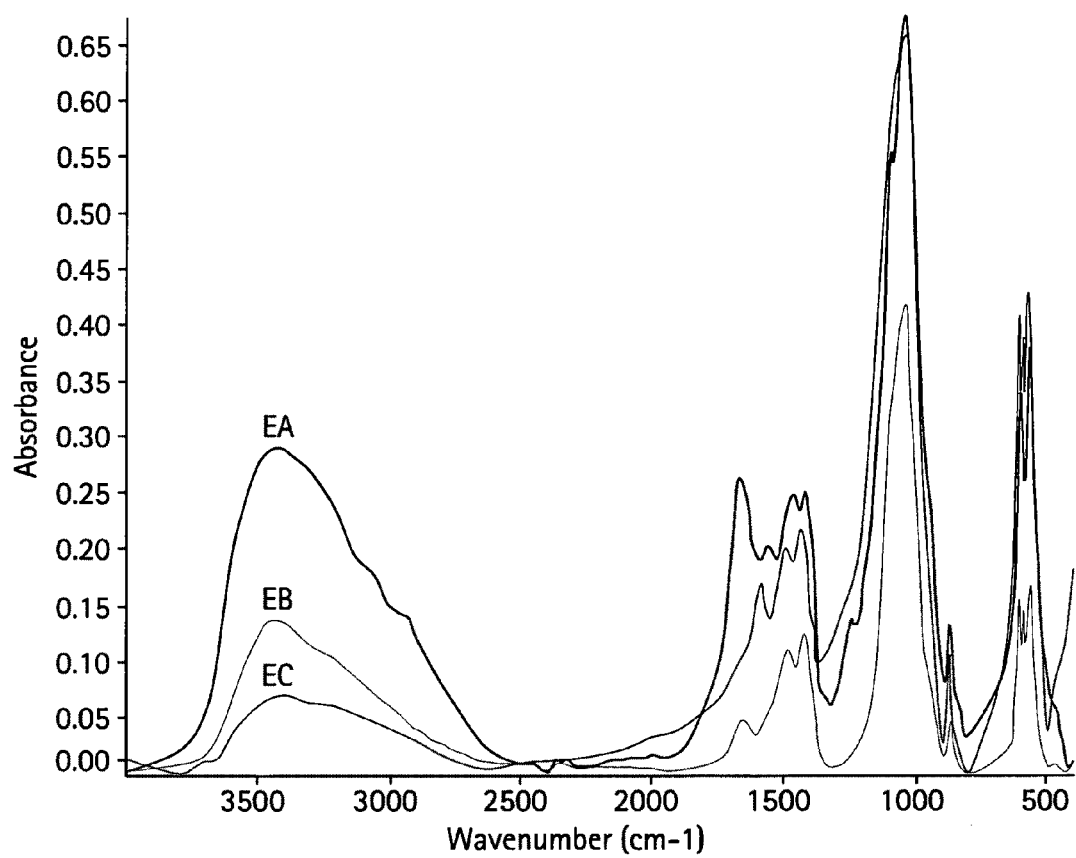
Figure 10A:
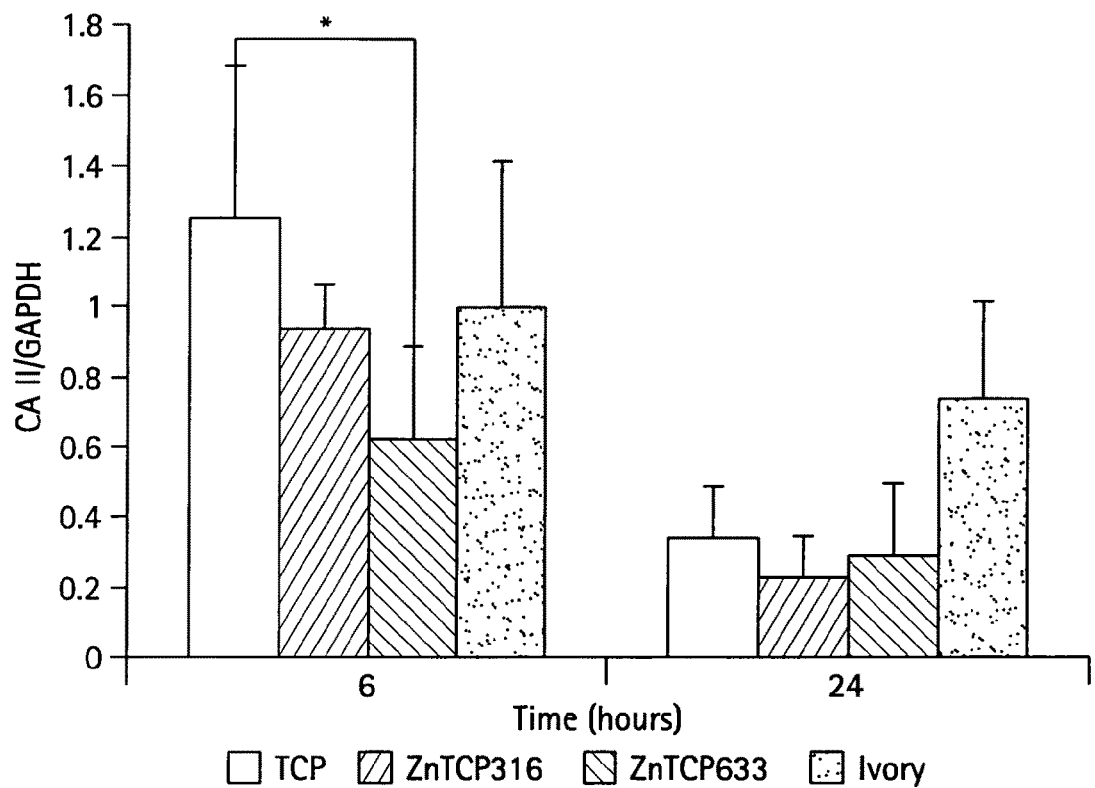
FIG. 10 demonstrates that Zn-TCP compared to β-TCP, suppressed the activity of mature osteoclasts through: (A) reduction in actin ring formation, (B) down-regulation of CAII and cathepsin K expressions without significant change in the expression of TRAP, and (C) increased cell apoptosis, in a dose dependent manner.
Figure 10B:
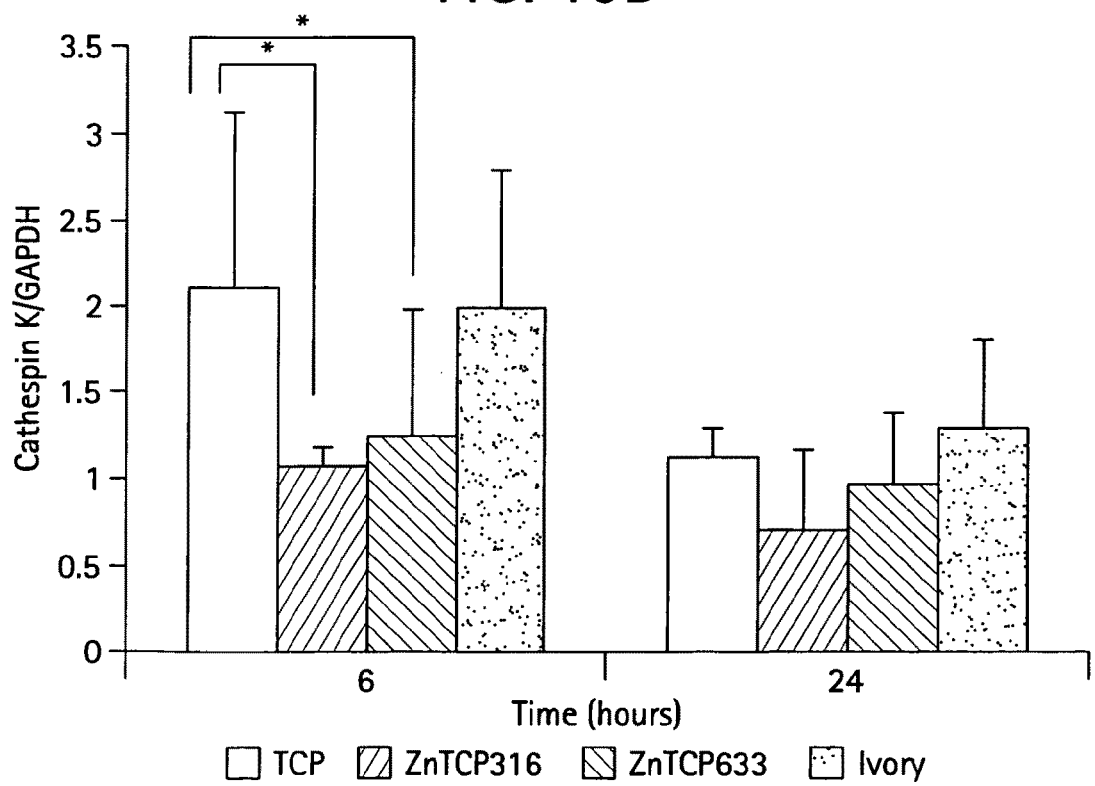
Figure 10C:
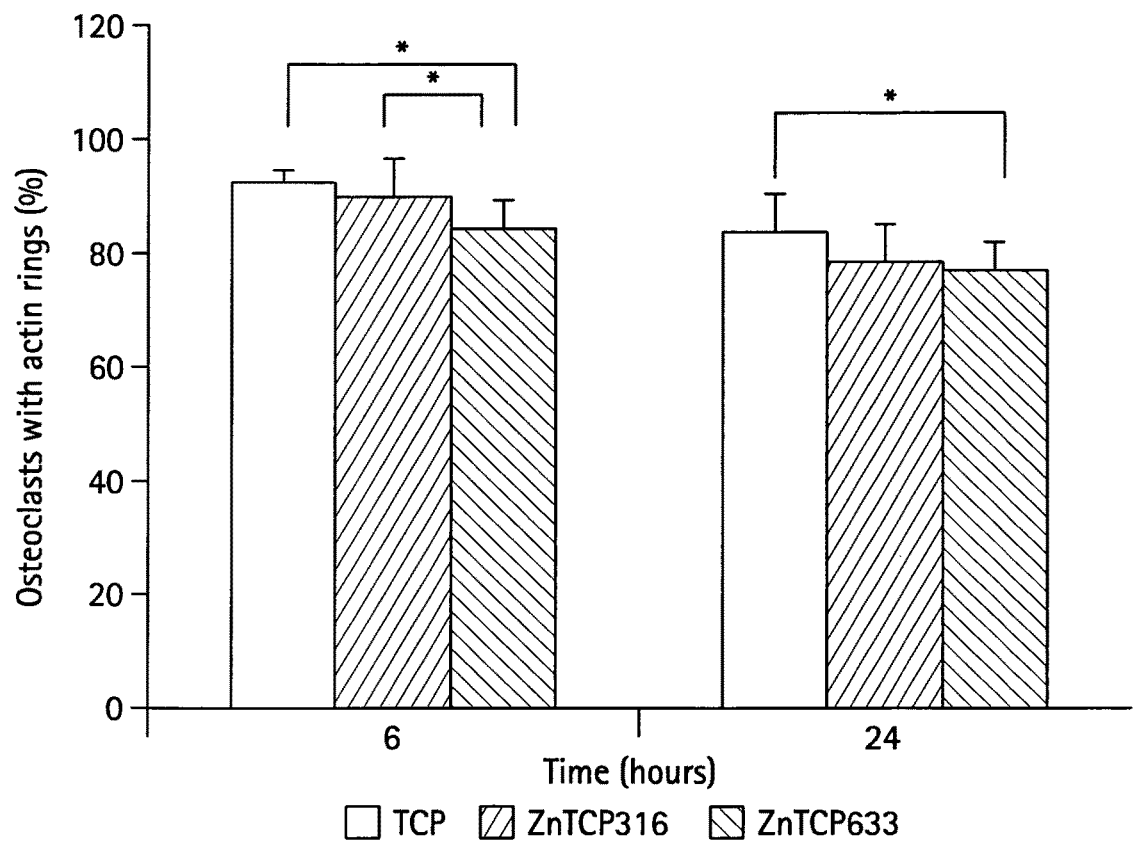

Results from in vitro studies demonstrated that MZF-CaPs (releasing Ca, P, Mg, Zn and F ions) promoted proliferation, differentiation and phenotypic expression of bone markers and protoglycans by osteoblast-like cells (bone forming) showing stimulation of bone formation (FIGS. 4,5,6). In vitro studies on osteoclasts showed that Zn—CaP (releasing Ca, P and Zn ions) and carbonate-F-apatite (releasing Ca, P and F ions) inhibited osteoclast (bone resorbing) activities (FIG. 10).

Mg, Zn, F simultaneously present at optimum concentrations in a calcium phosphate system (Mg/Zn/F—CaPs) enhance osteoblast activity (bone formation) as well as inhibit osteoclast activity (bone resorption) in vitro to a greater degree than when present separately. Cell response to materials with combined incorporation of Mg, Zn and F is more favorable than to materials incorporating these ions separately.

Ovariectomized Rat Model.

Ovariectomized rats have been used as an animal model for postmenopausal bone loss. The justification for this model is the observed similarities between ovariectomy-induced bone loss in rats and postmenopausal bone loss in humans, e.g., increased bone turnover, greater bone resorption than bone formation, greater loss of trabecular bone compared to cortical bone. The ovariectomized rats are given deficient diets to accelerate the onset of osteoporosis. Diet deficiency or immobilization and immobilization and calcium-deficient diet have been associated as risk factors for osteoporosis.

Prevention of Bone Loss by MZF-CaP Administered as Daily an Oral Supplement.

Figure 11:
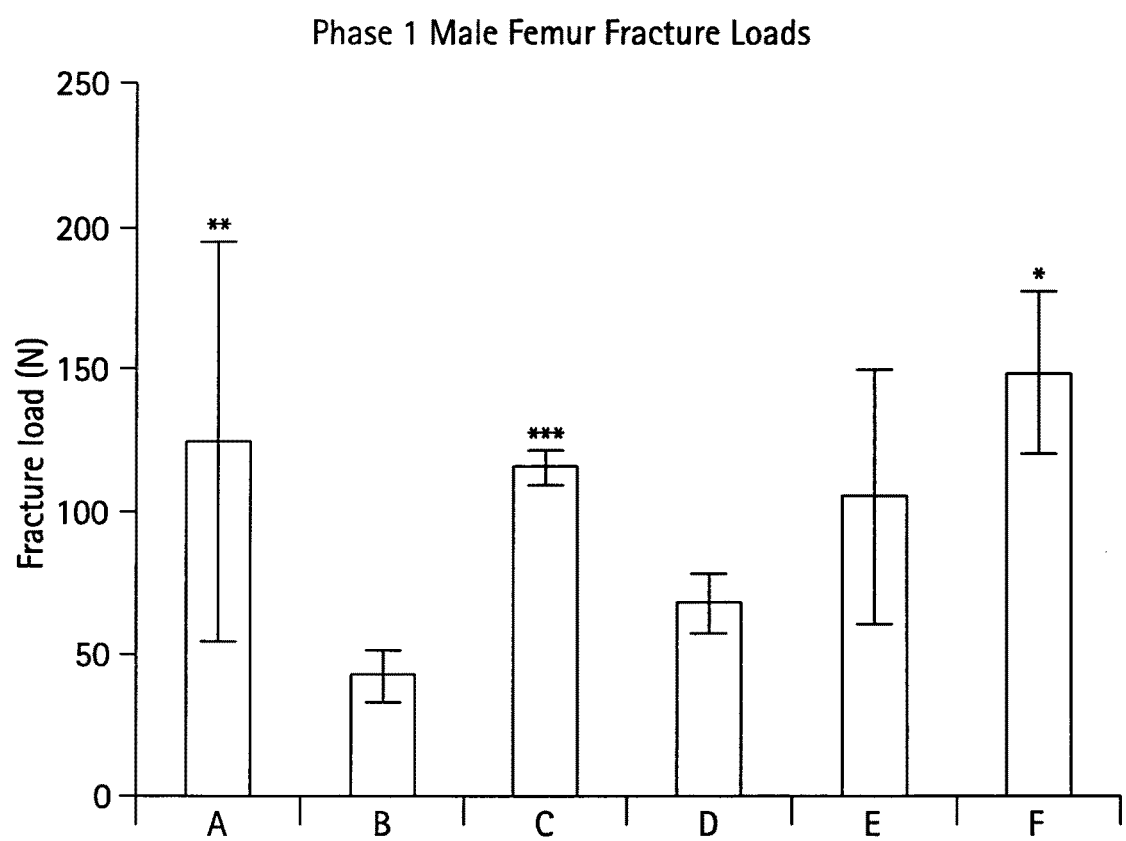
FIG. 11 represents bone fracture strength of femur of rats on (A) basic diet; (B) mineral deficient (MD) diet; on MD supplemented with: (C) Mg—CaP; (D) Zn—CaP; (E) F—CaP; and (F) MZF-CaP. Bone strength was significantly reduced by mineral deficient (MD) diet (B vs. A) and improved by the MZF-CaP supplemented diets (C,D,E,F vs. B).
Figure 13C:
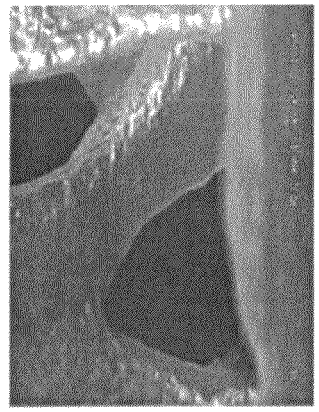
FIG. 13 shows SEM images of trabecular bone from rat on: (13A) basic diet; (13B) mineral deficient (MD) diet; (13C, 13D, 13E, 13F) MD diet supplemented with Mg—CaP, Zn—CaP, F—CaP and MZF-CaP, respectively. The trabecular bone loss induced by MD diet (13B vs 13A) was prevented by the supplemented diets (13C, 13C, 13E, 13F compared to 13B).
Figure 13B:
Figure 13A:
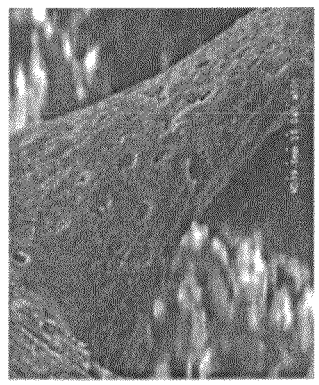
Figure 13F:
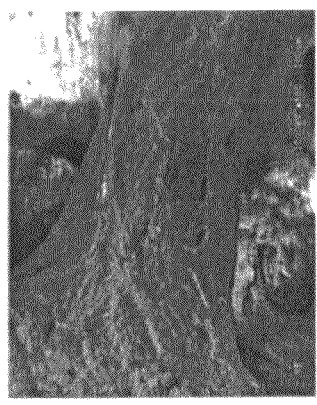
Figure 13E:
Figure 13D:

Results of initial studies demonstrated that mineral deficiency or estrogen deficiency (ovariectomy) in a rat model causes bone loss, thinning of cortical and trabecular bone, reduction in trabecular bone density and connectivity (FIGS. 12, 13) and decrease in bone strength (FIG. 11). All these features are similar to that observed in osteoporotic bone. The newly developed biomaterial, MZF-CaPs or synthetic bone mineral (SBM), when administered as a daily supplement to a mineral deficient diet or administered to OVX rats prevented bone loss in cortical and trabecular bones (FIGS. 12,13,16,17) (LeGeros et al, *Key Eng Mater* 2008; 361-363: 43-46; IADR 2006, abstract no. 270; IADR 2007, abstract no. 2176). The bone seeking ions (Mg, Zn and F) in MZFCaP were incorporated in the cortical and trabecular bones (Table 2).

TABLE 2

Composition (wt %) of rat cortical bones (not ashed). Phase 1.

| Diet | Ca | P | Mg | Zn | F |
|---|---|---|---|---|---|
| Basic | 26.44 | 12.121 | 0.50 | 0.05 | 0.02 |
| Mineral deficient (MD) | 25.77 | 11.96 | 0.26 | 0.05 | 0.02 |
| MD + Mg—CaP (#53) | 26/14 | 12/03 | 0.44 | 0.05 | 0.02 |
| MD + Zn—CaP(#54) | 25.93 | 11.78 | 0.31 | 0.24 | 0.02 |

TABLE 2-continued

Composition (wt %) of rat cortical bones (not ashed). Phase 1.

| Diet | Ca | P | Mg | Zn | F |
|---|---|---|---|---|---|
| MD + F—CaP(#52) | 25.87 | 11.62 | 0.40 | 0.08 | 0.21 |
| MD + MZF—CaP (#51) | 27.09 | 12.43 | 0.45 | 0.10 | 0.12 |

Prevention of Bone Loss by MZF-CaP Administered by Weekly Injection.

Parallel studies also showed that MZF-CaP administered as a weekly injection for 4, 12 or 16 weeks also increased bone strength (FIG. 14) and prevented bone loss induced by estrogen deficiency (Otsuka et al. *J. Pharm Sci* 2008; 97:421-432; *Key Eng Mater* 2006, 254-256:343-346; Tokudome et al., IADR 2006 abstract No. 1138).

Recovery of Bone Loss.

Figure 19A:
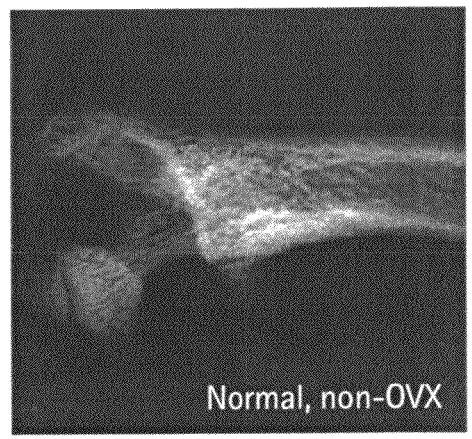
FIG. 19 shows Faxitron images of the femoral heads from (A) non-ovariectomized rats on a basic diet, (B) ovariectomized rats on a basic diet after two months, and (C) ovariectomized rats on a basic diet for two months then on basic diet supplemented with Mg/Zn/F—CaP supplements for one month. Bone loss induced by ovariectomy (B vs A) was recovered when the diet was supplemented with MZF-CaP was administered for one month (C vs B).
Figure 19B:
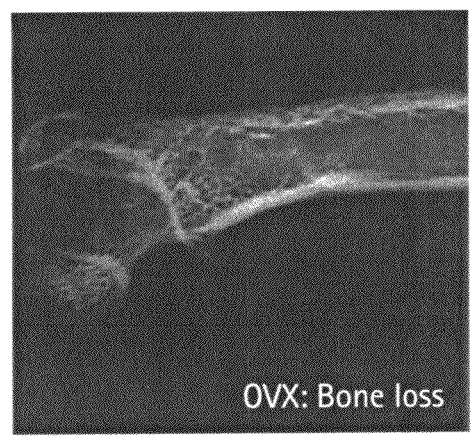
Figure 19C:
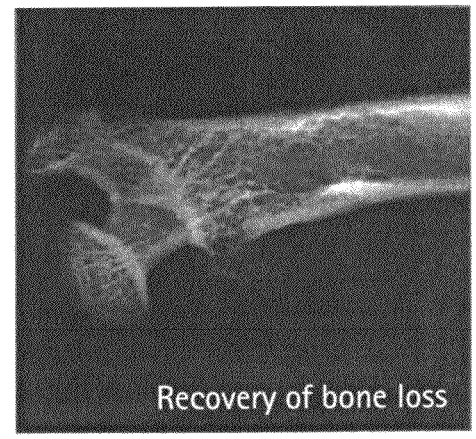
Figure 20A:
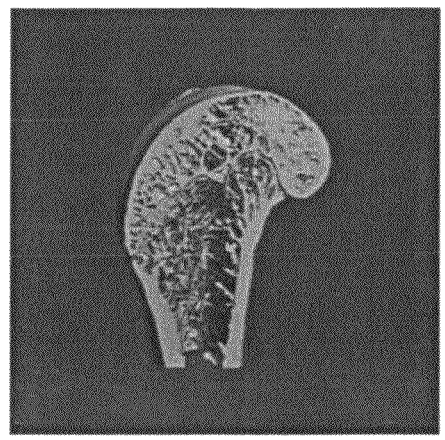
FIG. 20 shows microCT images of femur head demonstrating further the recovery of bone loss that may be achieved by providing Mg/Zn/F—CaP as a dietary supplement. MicroCT images of femur head of rat: (A) on a basic diet, (B) on a mineral-deficient diet for two months, and (C) on mineral-deficient diet for two months followed by a diet having a Mg/Zn/F—CaP dietary supplement for one month. The bone loss induced by mineral deficiency (B vs A) was recovered by adding MZF-CaP supplement to the mineral-deficient diet for one month (C vs B).
Figure 20B:
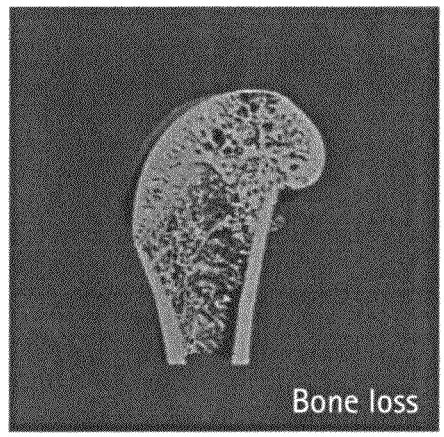
Figure 20C:
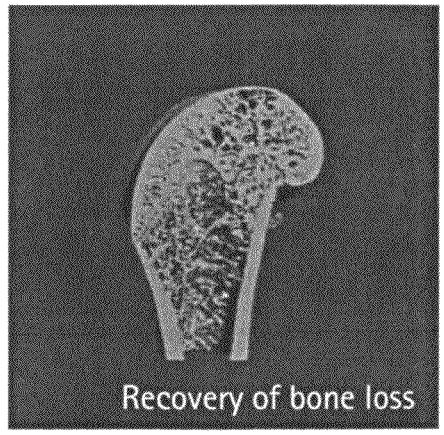

Current FDA approved drugs have been shown to prevent further bone loss but were not shown to recover or restore bone already lost to the disease (Mohan et al., (1996) In: Principles of Bone Biology Ch 80 Academic Press: New York, pp. 1111-1124). These preliminary results demonstrate that MZF-CaP administered as oral supplement restored bone loss induced by either mineral deficiency or estrogen deficiency (ovariectomy) as shown in FIGS. 19 and 20.

Dissolution Properties of Rat Bones.

Figure 18:
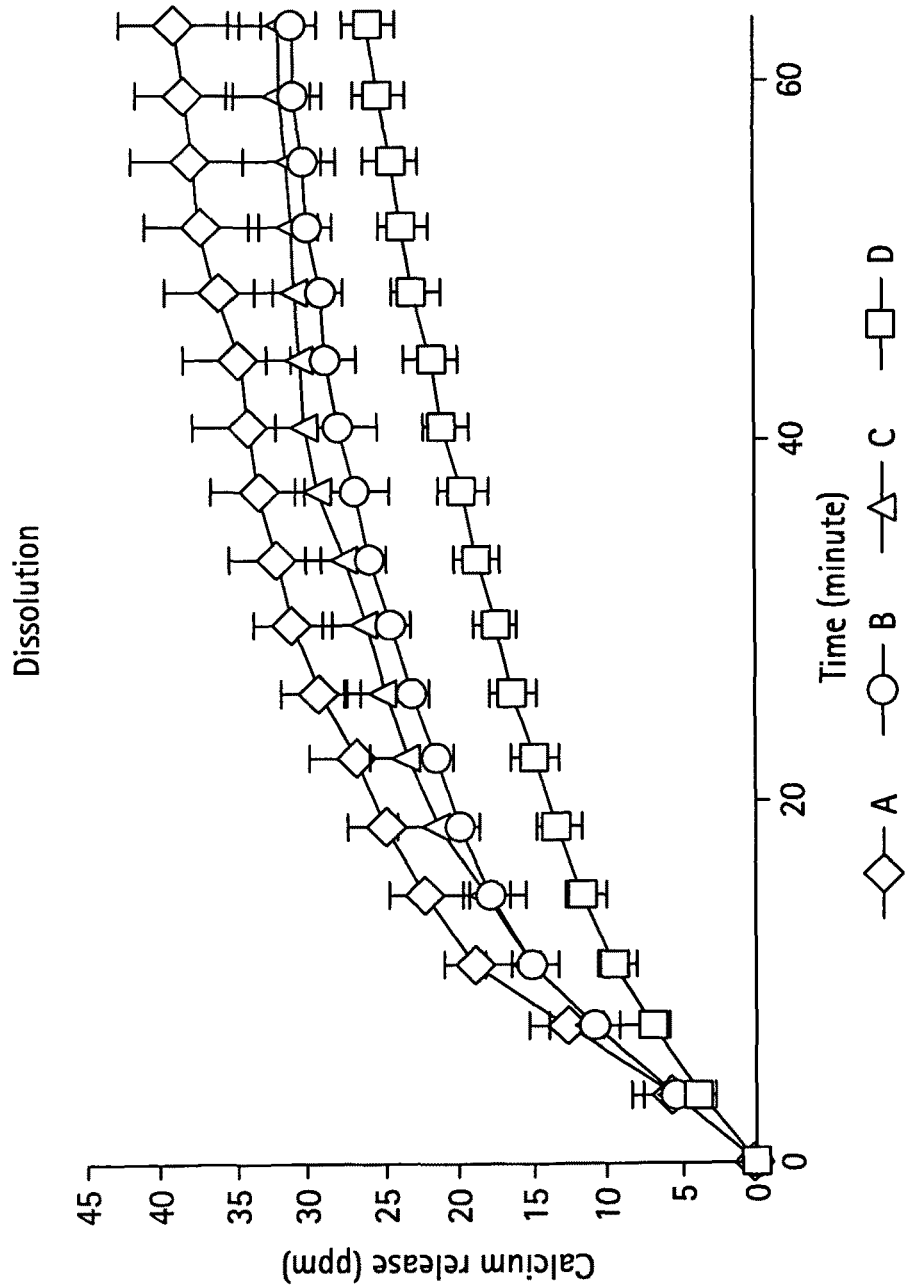
FIG. 18 depicts the extent of dissolution (expressed as release of $Ca^{2+}$ ions with time) of rat bones in acidic buffer (0.1M KAc, pH 6 at 37° C.). The dissolution is lower in bones from OVX and non-OVX rats on a basic diet supplemented with MZF-CaP (B vs. A; D vs. C).

Osteoclastic activity results in bone resorption. Such activity occurs in an acidic environment. In vitro dissolution (in acidic buffer) rates of bone obtained from animals receiving MZF-CaP supplement were shown to be lower than those from controls (not receiving MZF-CaP supplement untreated) as shown in FIG. 18. Treatment results in compositional changes in the bone mineral making it less susceptible to acid challenge (bone resorption)

EXAMPLES

The following examples are provided to further demonstrate particular embodiments of the invention and are not considered to limit the scope of the invention.

Example 1

Cell Response to Mg/Zn/F-BCP Materials

Unsintered materials used for studies on in vitro cell response included Mg—CaP, Zn—CaP, F—CaP, Mg/Zn/F—CaP.

Effect on Proliferative Capacity of Osteoblast-Like (Bone-Forming) Cells.

The effect on the proliferative capacity of human osteoblast-like cells was studied by incubating human MG-63 ($10^5$ cells/well/ml) in the presence or absence of materials at 37° C., 5% $CO_2$ for 5 days. The cells were radiolabeled with 1 mCi of $^3$H-thymidine, and the proliferation rate was determined by scintillation counting of TCA precipitable DNA. The materials significantly increased the proliferative capacity of osteoblast-like cells. Higher proliferative effect compared to control in cells exposed to the synthetic materials was observed.

Effect on Phenotype Expression of Bone Growth Markers.

The effect on the phenotype expression and growth markers of human bone-derived osteoblasts was studied by incubating $10^5$ cells/well/ml in the presence or absence of the materials at 37° C., 5% $CO_2$ for 5 days. Total RNA was isolated and specific transcript levels for osteocalcin (OSC), alkaline phosphatase (AP), collagen type I (Col 1), osteopontin (OSP) and growth markers cyclin D1 (CD1) and CDk5 were determined by reverse transcriptase polymerase chain reaction (RT-PCR). The levels of OSC mRNA were low and expression was not detectable in osteoblasts incubated in control medium alone. Incubation with four different preparations enhanced OSC expression to detectable level (FIG. 5). OSC is documented to play a critical role in mineralization.

FIG. 5 depicts the effect of the present synthetic materials on proliferation of human osteoblast-like cells (MG-63) compared to control. All the materials, especially (2), (4), (5) and (6) caused increased cell proliferation compared to control. (1) and (6) have similar F concentrations, (1) has lower Mg and Zn concentrations. FIG. 6 shows the effect of the present synthetic materials on the phenotype expression: osteocalcin, OSC; alkaline phosphatase, AP; collagen type I, Col I; and osteopontin, OSP and growth markers: cyclin D1 (CD1) and CDk4. OSC becomes detectable from materials (4), (5) and (6). The expression for OSP is stronger for materials (4), (5) and (6). The materials used for both tests: (1) Mg/Zn/F—CaPa, (2) Mg/CHA, (3) Zn/CHA, (4) CHA, (5) CFA, and (6) Mg/Zn/F—CaPb. (1) and (6) have equivalent levels of F and $CO_3$, Mg and Zn levels lower in (1) compared to (6). The levels of Mg in (2) and that of Zn in (3) are equivalent to that in (6). The levels of F in (1), (4) and (6) are similar and the levels of $CO_3$ in (10 to (6) are similar. MZF-CaPs also affect the human osteoblasts expression of proteoglycans. Analysis of proteoglycan transcripts showed no distinct pattern in versican expression whereas decorin expression appeared to be modulated by the CaPs. Biglycan expression was profoundly increased by CaPs containing Mg, Zn and F.

Example 2

Preparation and Characterization of Unsintered and Highly Sintered (Ceramic) Materials Incorporating Mg, Zn, and F in a Calcium Phosphate Matrix The materials are designated herein as Mg/Zn/F—CaP. Mg/Zn/F—CaP will consist of one phase (Mg-, Zn- and/or F-substituted carbonate apatite) or of biphasic calcium phosphate, BCP, an intimate mixture of β-TCP (Mg- and Zn-substituted) and carbonate apatite (Mg-, Zn- and F-substituted). (Mg, Zn, F and Ca have been separately associated with bone formation, bone resorption, biomineralization).

Studies on synthetic and biologic apatites (mineral phases of enamel, dentin and bone) using a combination of analytical techniques (x-ray diffraction, infrared spectroscopy, chemical analysis) demonstrated that biologic apatites (the mineral phases of enamel, dentin, cementum and bone) are not pure hydroxyapatite, $Ca_{10}(PO_4)_6(OH)_2$ (stoichiometric Ca/P molar ratio, 1.67) but are associated with minor constituents (most important of which are magnesium and carbonate) and trace elements. Therefore, biologic apatite such as bone apatite, may be more accurately described as carbonate apatite, approximated by the formula: $(Ca,Mg,Na)_{10}(PO_4,CO_3,HPO_4)_6(OH,Cl,F)_2$ where Mg, Na and $CO_3$ are minor constituents and Cl and F may be present in trace amounts. Substitutions or incorporation of different ions in the apatite lattice cause changes in properties: lattice parameters, crystallinity (reflecting crystal size or perfection), and solubility. For example, partial $CO_3$-for-$PO_4$ substitution (coupled with Na-for-Ca substitution) or partial Mg-for-Ca substitution causes an increase in solubility and decrease in crystallinity. Mg and $CO_3$ have synergistic effects on the properties of apatite. F-for-OH substitution causes a decrease in solubility and increase in crystallinity of synthetic and biologic apatite and promotes formation of less Ca-deficient synthetic apatites. Pure β-TCP cannot be obtained from solution. However, when Mg or Zn ions are present, Mg- or Zn-substituted β-TCP are formed. The formation of partially substituted Mg or Zn in apatite or in β-TCP or Mg- or Zn-containing amorphous calcium phosphate (ACP) depends on the solution Mg/Ca or Zn/Ca or (Mg+Zn)/Ca molar ratios.

Mg- and Zn-deficiencies have been implicated as risk factors in the development of osteoporosis. Separately, Mg, Zn or F has been recommended for osteoporosis therapy. Also, separately, these ions have also been shown to promote bone formation and increase bone mass. In rats, at the biologic apatite crystal level, Mg supplementation was shown to cause the formation of smaller bone apatite crystals and smaller enamel apatite crystals while F-incorporation in bone from the drinking water caused the formation of larger and less soluble bone apatite crystals. F has been shown to consistently increase bone mass. However, other studies have reported increased bone fracture with prolonged use of F compounds. F was shown to affect the orientation of collagen and decrease the level of collagen synthesis, modify bone matrix components and was associated with abnormal mineralization. On the other hand, Zn ions were shown to increase collagen and DNA synthesis.

The material of the present invention, by combining relatively optimum concentrations of F, Mg and Zn ions in a calcium phosphate matrix, combines the beneficial effects of F of these ions on the bone mineral (increasing crystallinity and decreasing solubility) and of Mg and Zn on the organic matrix components thus minimizing deleterious effects of Mg and/or Zn on the bone mineral or deleterious effect of F on bone matrix components. In addition, since these ions appear to act additively or synergistically, the dose for each ion can be reduced to a level that will not be harmful after prolonged use.

Example 3

Preparation and Characterization of Uncalcined or Unsintered Material Incorporating Mg+F (M/F—CaP), Zn+F (Zn/F—CaP), and Mg+Zn+F (Mg/Zn/F—CaP) in a Calcium Phosphate Matrix Materials and Methods.

All chemicals used in the preparation of MZF-CaPs or SBM were reagent grade (Fischer Chemicals, New Jersey). MZF-CaP or SBM were prepared by hydrolysis method. Preparations incorporating only Mg, (MgCaP) or Zn (Zn-CaP), F (FCaP) and all three ions (MZFCaP) in a calcium phosphate matrix were made. The preparations were characterized using Xray diffraction (X'Pert, Philips), FTIR (Nicolet 500), thermogravimetry, TGA, and inductive coupled plasma, ICP (ThermalJarrel Ash) for Ca, Mg, Zn, P, Na contents; and F for F ion selective electrode.

Figure 1:
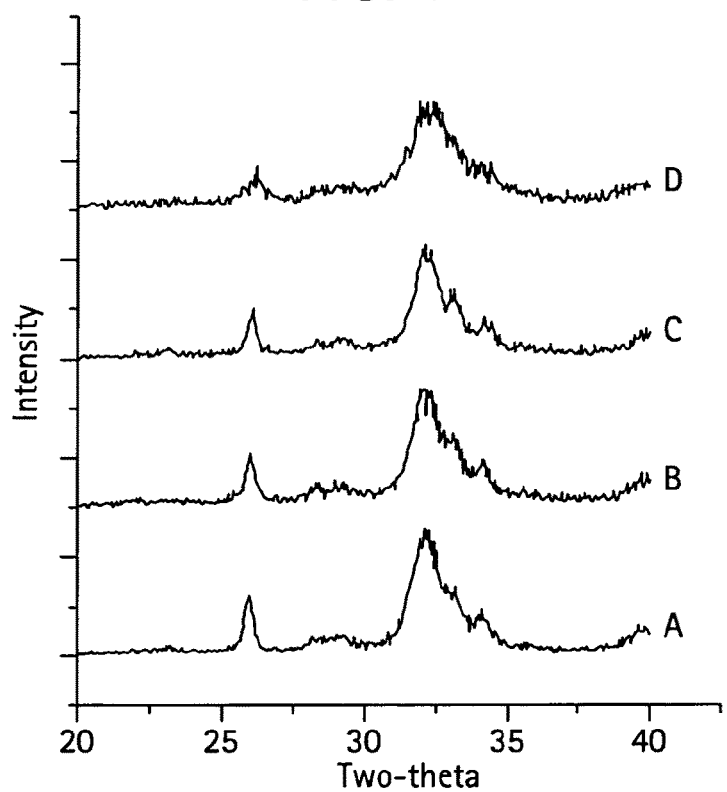
FIG. 1 shows XRD patterns of precipitated carbonate apatite which has been substituted with ion combinations in accordance with the invention. XRD patterns of precipitated carbonate apatite containing: (A) F, (B) Mg+F; (C) Zn+F; and (D) Mg+Zn+F. The differences in the sharpness of the diffraction peaks (line broadening) at about 25.8° 2Θ reflect the difference in their crystallite size. Mg and Zn have additive effects on reducing crystallinity of apatite (B & C vs D).
Figure 2:
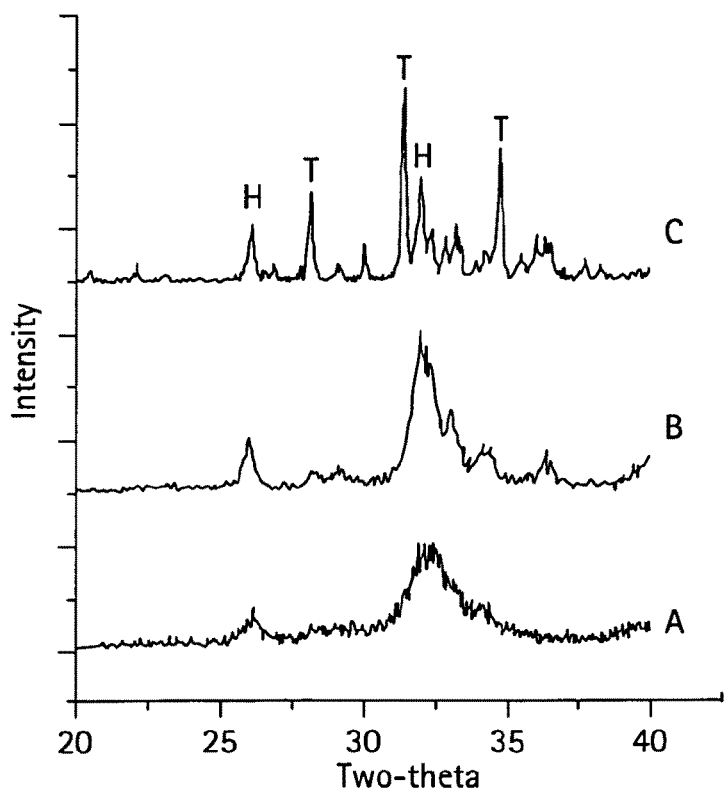
FIG. 2 shows XRD patterns of Mg/Zn/F—CaP: (A) before and after sintering (B) at 600° C.; and (C) at 800° C. T=Mg- and Zn-substituted β-TCP; H=F-substituted apatite.

The MZFCaP or SBM preparations showed XRD profiles shown in FIGS. 1 and 8. F—CaP, MgCaP and CaP incorporating all three ions, MZFCaP showed only the apatite XRD profiles, with FCAP showing the higher crystallinity (larger crystalsize); while Zn—CaP showed two phases: Zn-substituted tricalciumphosphate (Zn-CP) and apatite. The composition of these preparations is listed in Table 1.

Ca and P ion concentrations were not significantly different in bones of rats in all diets. However, Zn ion concentration was highest in bone from rats given mineral deficient (md)+Zn—CaP; F ion concentration highest in bones given F—CaP and MZF-CaP; Mg ion concentration was lowest in bones of rats on md diet and not significantly different in bones of rats on normal or supplemented diets. (Table 2). The crystallinity (reflecting crystal size) of bones from rats on basic or supplemented diets were significantly higher (larger crystal size) than those from rats on mineral deficient diets.

Example 4

The release of ions (Ca, Mg, Zn and P) in acidic buffer (0.1M Kac, pH 6, 37 C) with time, depends on the composition of MZF-CaP. With similar $CO_3$ concentrations, the higher the F concentration, the lower the rate of release, the higher the Mg and Zn concentrations, the higher the rate of release (FIGS. 3 and 4). Compared to OTC (over the counter) calcium supplements (e.g., CALTRATE® or calcium carbonate) that only released Ca ions in larger amounts at a shorter time, MZF-CaP simultaneously released Ca, P, Mg, Zn and F ions.

High Temperature (800° C. to 1100° C.) Preparations.

Figure 9A:
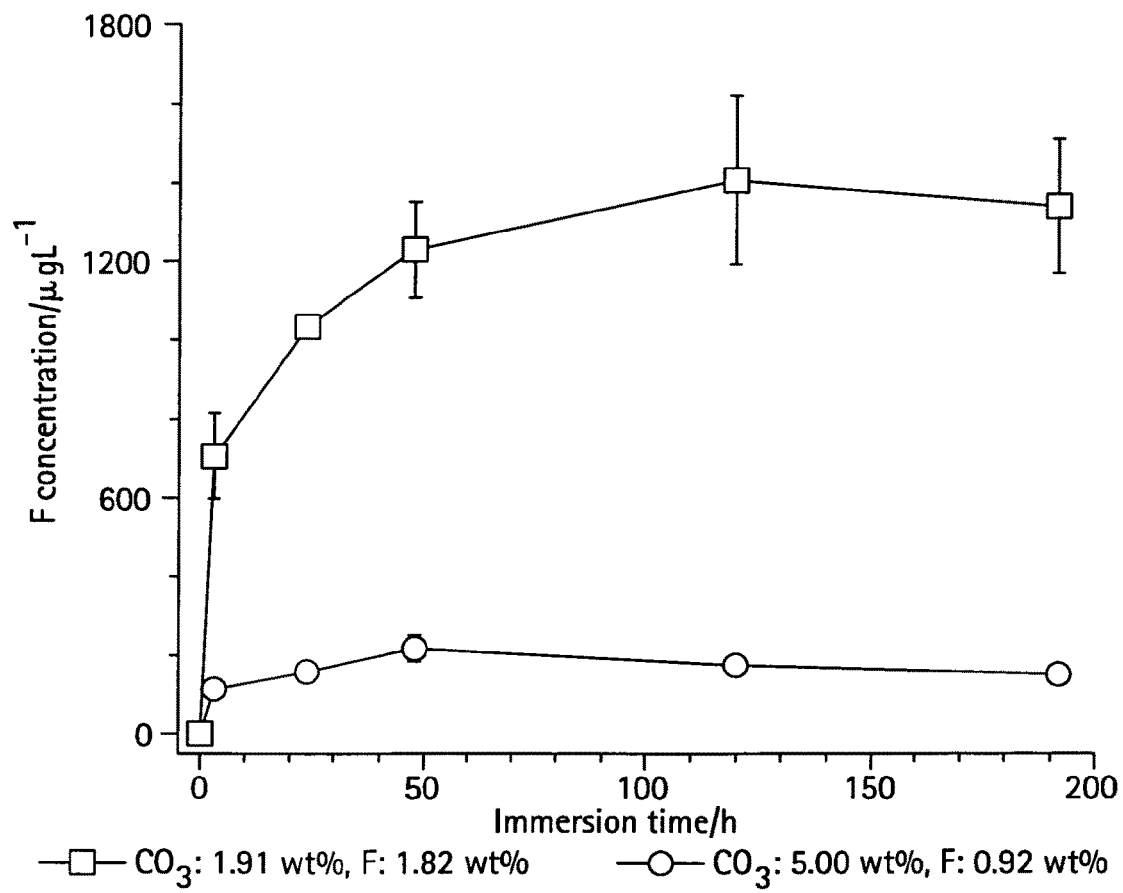
FIG. 9 shows dissolution expressed as release of $Ca^{2+}$ ions with time from: (A) F—CaP containing high and low concentrations of F; (B) Mg-TCP; and (C) Zn-TCP. (B) and (C) contain different levels of Mg or Zn, respectively. Dissolution rates of Mg-TCP and Zn-TCP decrease with increasing Mg (B) or Zn (C) and dissolution rate of F—CaP decreases with increasing F (A).

The conditions for high temperature preparation of F-containing carbonate apatites (CFA), Mg-substituted β-TCP (Mg-TCP) and Zn-substituted β-TCP (Zn-TCP) were optimized. Determination of some of the chemical properties (composition, dissolution properties) showed the following: (a) CFA prepared at high temperatures (800° C.) containing high F and low $CO_3$ contents had lower dissolution rate than that with low F and high $CO_3$ (FIG. 9A) confirming results obtained with CFA's prepared at low temperatures (95° C.); (b) increasing amounts of Mg or Zn in the β-TCP decreased their dissolution rates (FIGS. 9B,9C) similar to that observed with Mg-TCP prepared at low temperature.

Example 5

Determination of In Vitro Cell Response to MZF-CaPs

Osteoblast-Like Cell Response.

More than forty MZF-CaP formulations were screened for their effect on the (i) proliferative capacity, (ii) type I collagen production and (iii) phenotype expression of bone markers of osteoblast-like cells (MG-63). Response of osteoblast-like cells on all the MZF-CaPs tested showed increased proliferation, higher production of type I collagen and phenotypic expression of bone markers, including alkaline phosphatase, extracellular matrx (ECM) constituents such as alkaline phosphatase, type I collagen, osteocalcin and proteoglycans.

Inhibitory Effect of Zn-TCP on Osteoclastic Activity.

10-day-old Japanese white rabbits were used in this study. Cell response to β-TCP with increasing amounts of Zn was determined from formation of an actin ring and expression of the following genes analyzed by quantitative RT-PCR: carbonic anhydrase II (CAII), cathepsin K/OC2, TRAP and glyceraldehydes-3-phosphate dehydrogenase (GAPDH). The resorbing activity of osteoclasts was assessed by measuring the morphological parameters of resorption pits. Results showed that Zn-TCP compared to β-TCP, suppressed the activity of mature osteoclasts through reduction in actin ring formation (FIG. 10A), down-regulation of CAII and cathepsin K expressions (FIG. 10B) without significant change in the expression of TRAP and increased cell apoptosis (FIG. 10C), in a dose dependent manner.

Example 6

Determine the Effect of Orally Administered Various Mg/Zn/F—CaPs on Bone Properties of Mineral Deficient Rats Sprague-Dawley rats (Charles River Labs), 2 months old (average weight, 165 g) were randomly distributed into the following groups (10 per group for female or male rats): GA: on basic diet; GB: on mineral deficient diet (MD); GC: on MD diet+Mg—CaP; GD: MD diet+Zn—CaP; GE: MD diet+F—CaP; and GF: on MD+Mg/Zn/F—CaP (MZF-CaP) for 3 months. Rat food pellets (basic, mineral deficient and supplemented mineral deficient diets) were prepared by Purina Test Diets. Compositions of the MZF-CaP preparations and of the diets are summarized in Tables 1 and 3, respectively. Animal protocol was approved by NYU IUCAC and adhered to the NIH guidelines for the care and use of laboratory animals. The rats were sacrificed by $CO_2$ inhalation. The bones (femurs, tibias, vertebras, jawbones) were separated, cleaned of soft tissues and stored according to type of analyses: femurs for bone strength analyses were wrapped in wet gauze and directly frozen; other bones were stored in 70% alcohol and stored at °20° C. Bones for x-ray diffraction (X'Pert Philips), SEM (Hitachi S3500N), radiography (Faxitron Series 43805 N X-ray System, Hewlett-Packard), and microcomputed tomography, microCT (µCT 40, Scanco Medical, Switzerland). Tibias for compositional analysis (by inductive coupled plasma for Ca, Mg, Zn, and P and by F-ion selective electrode for F) were ashed at 600° C. Other tibias were enzyme treated and analyzed as unashed samples. Composition of unashed cortical bone is summarized in Table 2. Bone strength (FIG. 11) was determined by 3-point bending using universal testing machine (Instron). SEM images showed that mineral-deficient (MD) diet caused thinning of the cortical bone (FIG. 12B), and MD diet supplemented with Mg—CaP (FIG. 12C), Zn—CaP (FIG. 12D), F—CaP and especially (FIG. 12E), MZF-CaP (FIG. 12F), prevented bone loss. Similar effects on trabecular bone thickness (FIG. 13), bone density and trabecular bone connectivity were observed.

TABLE 3

Composition of the diets given to the rats.

| Diet | wt % Ca | wt % P | wt % Mg | ppmZn | ppmF |
|---|---|---|---|---|---|
| Basic | 0.6 | 0.57 | 0.07 | 21 | 0.0 |
| Mineral deficient(MD) | 0.0 | 0.0 | 0.17 | 0.0 | 0.0 |
| MD + Mg—CaP(#53) | 0.17 | 0.29 | 0.07 | 1.0 | 0.0 |
| MD + Zn—CaP | 0.17 | 0.21 | 0.0 | 370 | 0.0 |
| MD + F—CaP | 0.19 | 0.27 | 0.0 | 0.0 | 67.2 |
| MD + MZF—CaP | 0.18 | 0.27 | 0.02 | 276 | 66.3 |

Example 7

Prevention of Bone Loss Induced by Ovariectomy

Non-OVX and OVX Sprague-Dawley rats (3 months old, average weight, 225 g) were distributed into the following groups: G1: control (non-Ovx Rats); G2: OVX rats on basic diet (BD); G3: OVX rats on BD supplemented with MZF-CaP for 5 months. After sacrifice, femurs, tibia, vertebra, and jawbones were collected, cleaned of extraneous tissues and stored according to what type of analyses will be performed. Mechanical test (3-point bending) were determined using femurs. TGA, XRD and FT-IR analyses were made on tibia and vertebra, SEM and microCT on femurs that were cleaned of extraneous soft tissues; Ca, P, Mg, Zn, Na and F determinations were made on ashed (800° C.) bones. Faxitron, (radiography), SEM and microCT images showed that bone loss induced by estrogen deficiency was prevented when diet was supplemented with MZF-CaP. Results from these studies demonstrated that MZF-CaPs administered daily as supplement to mineral deficient or basic diets were effective in preventing bone loss enhancing bone strength induced by mineral deficiency or estrogen deficiency (ovariectomy) in rats.

Example 8

Determine Therapeutic Effect of MZF-CaP Administered by Weekly Injection on Ovariectomized Rats on Enhancing Bone Properties (Bone Density and Bone Strength)

Figure 14A:
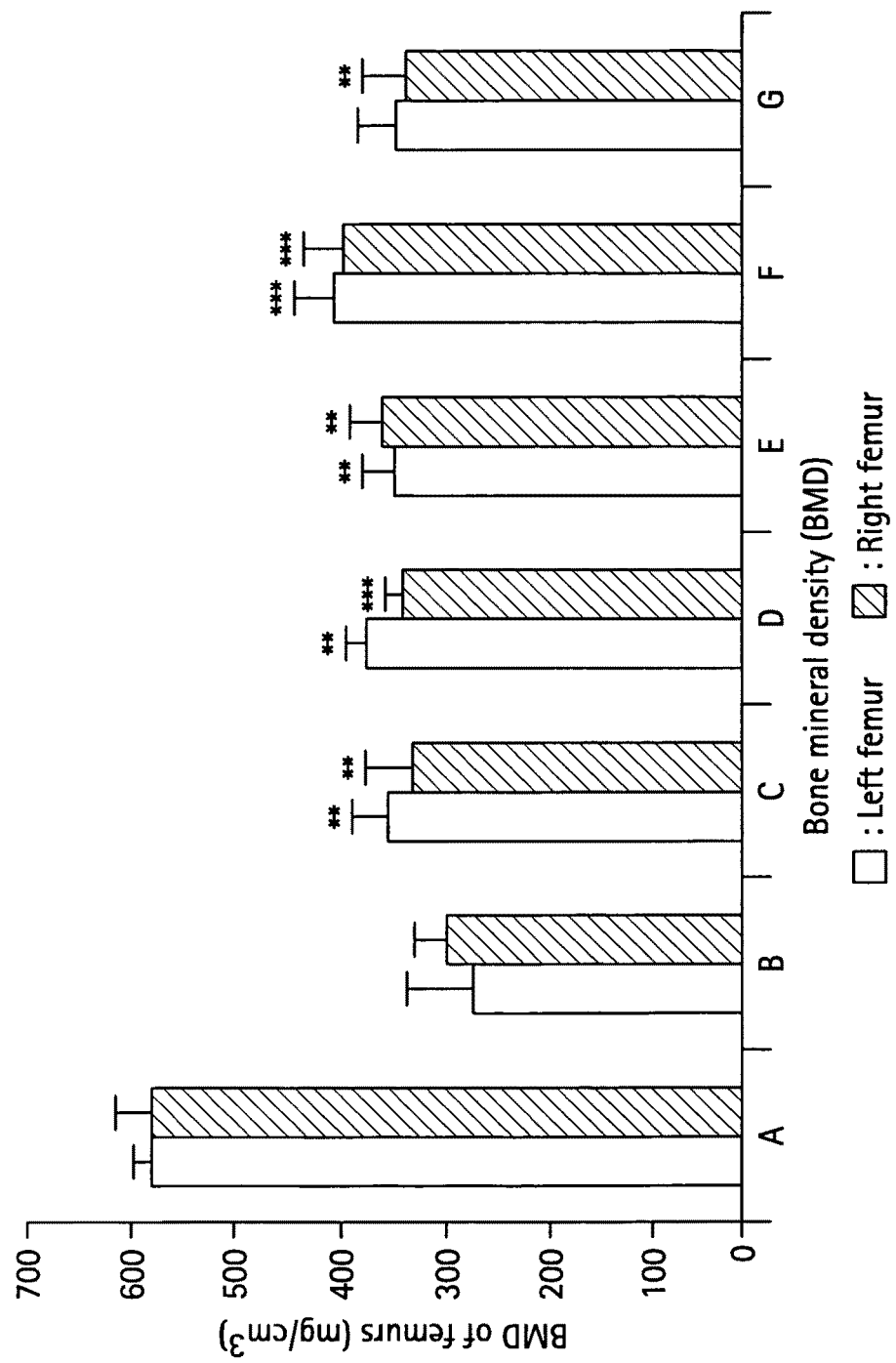
FIG. 14 depicts bone mineral density, BMD of left and right femurs of (A) non-OVX, (B) OVX, (C) OVX injected with Zn-TCP; and OVX injected with MZF-CaPs (D,E,F,G) Ovariectomy induced reduction in BMD (B vs. A), injection with MZF-CaPs prevented the loss in BMD (D,E,F, G compared to B) (14A) Wistar rats after 12 weeks. (14B) Sprague-Dawley rats after 16 weeks.

Sprague Dawley rats (4 weeks old) were used. The rats were randomly assigned to 6 groups (6 rats per group): GN—normal (non-OVX); GC: control (OVX rats on Zn-deficient diet); G1, G2, G3 and G4 were OVX. Rats receiving weekly injections of Zn-TCP (G1), MZF-CaP #51 (G2), MZF-CaP#68 (G3) and MZF-CaP#76 (G4). The compositions of these MZF-CaPs are listed in Table 1. The composition of Zn-TCP: 6.17 wt % Zn; 34.1 wt % Ca and 19.5 wt % P. 10 mg of MZF-CaP or Zn-TCP in 0.1 mL saline solution was injected intramuscularly in the right thighs of the OVX rats in all groups once a week for 12 weeks and 16 weeks. Results showed that the bone mineral densities (BMD) of the treated groups (G1 to G4) were greater than the OVX groups (GC) (FIG. 14).

Example 9

Determine the Effect of MZF-CaP Supplement in Preventing Bone Loss Induced by Estrogen Deficiency (Ovariectomy)

Figure 15:
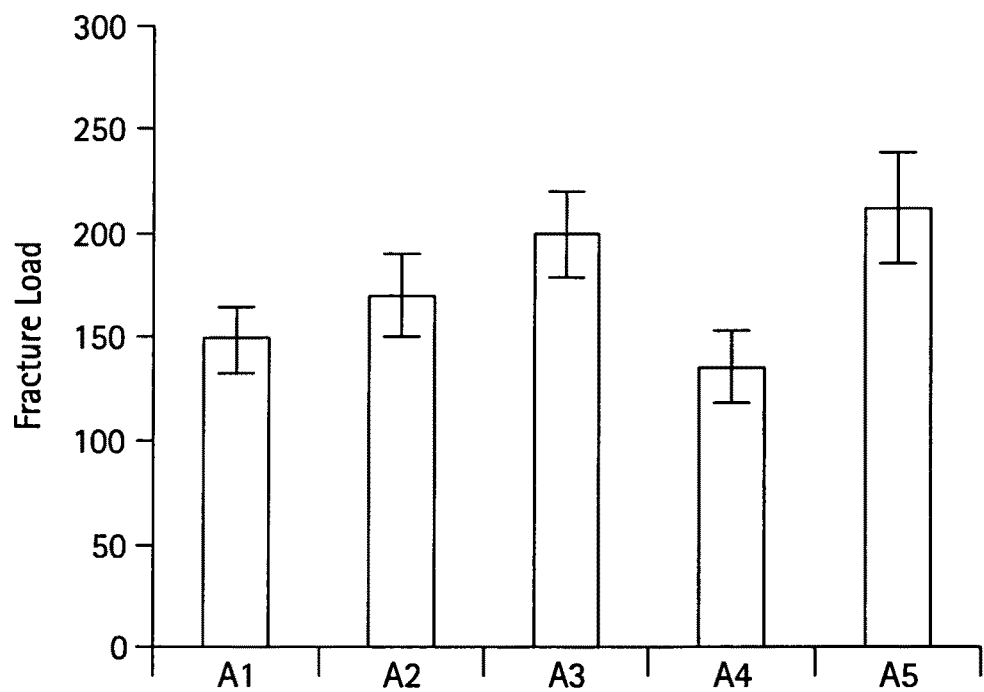
FIG. 15 depicts bone strengths of OVX rats on (A1) basic (BD) for 3 months; (A2) BD, 3 months, then BD+MZF-CaP for 2 additional months; (A3) BD+MZF-CaP for 5 months; and non-OVX on (A4) BD for 5 months; and (A5) BD+MZF for 5 months showing increased bone strength in bones from rats (OVX or non-OVX) on diet supplemented with MZF-CaP.
Figure 16A:
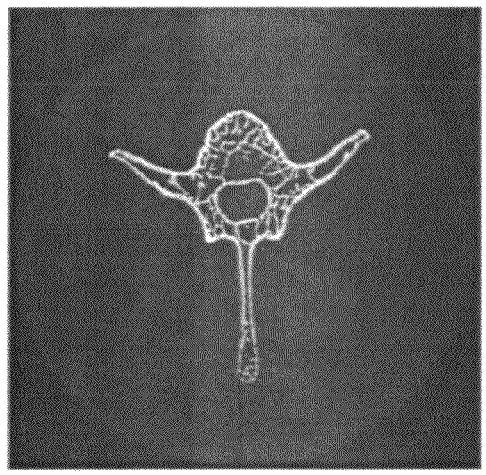
FIG. 16 shows microCT images of L-5 vertebra (one slice, 10μ) from: (A) OVX rat on basic diet, 5 months; and (B) OVX rat on basic diet supplemented with MZF-CaP showing prevention of bone loss induced by ovariectomy or estrogen-deficiency (16B vs 16A).
Figure 16B:
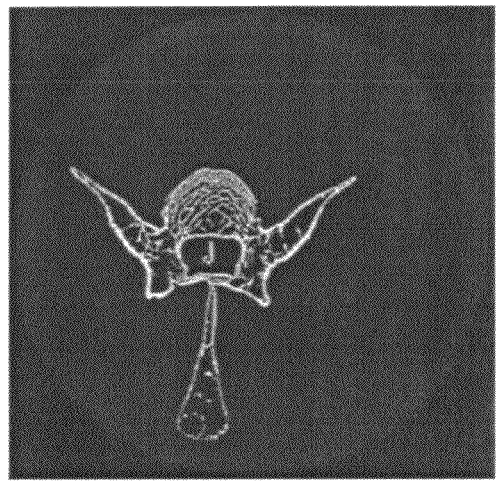
Figure 17A:
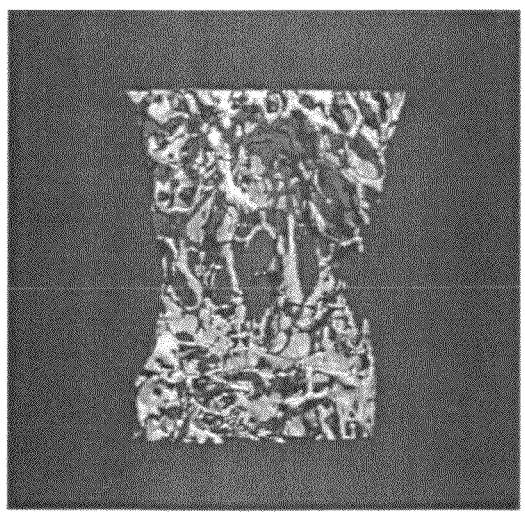
FIG. 17 shows microCT images of L-5 vertebra (261 slices, 10μ/slice, standard resolution) of OVX rats on (A) basic diet, and (B) basic diet supplemented with MZF-CaP MZF-CaP increased bone volume, trabecular thickness and decreased bone porosity.
Figure 17B:
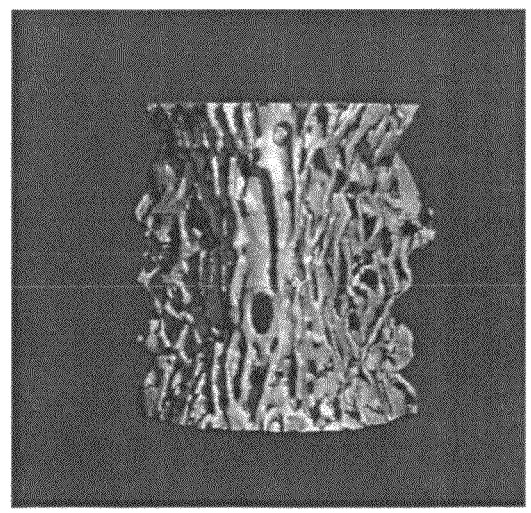

Non-OVX and OVX Sprague-Dawley rats (3 months old, average weight, 225 g) were randomly distributed in the following groups (4 rats per group): G1: control (non-Ovx rats) on basic diet (BD), 5 months; G2: non-OVX rats on BD+MZF-CaP (#74); G3: OVX rats on BD for 3 months, then BD+#74 for 2 months; G4: OVX rats on BD supplemented with MZF-CaP, 5 months. Improved bone strength (FIG. 15), improved microarchitecture (FIG. 16B vs 16A; 17B vs 17A), and decreased susceptibility to acid dissolution in acidic buffer (FIG. 18) were observed in bones from rats with basic diets supplemented with MZF-CaP. In a continuing study, the effect of MZF-CaP (with low fluoride) and of MZ-CaP/FF on preventing bone loss induced by ovariectomy will be evaluated using larger number of rats and correlating bone strength with bone quality.

FIGS. 19 and 20 represent the effect of Mg/Zn/F—CaP dietary supplements on recovery of bone loss induced by estrogen deficiency (ovariectomy) in rats. FIG. 19 represents microCT images of the femoral heads from (A) non-ovariectomized rats on a basic diet, (B) ovariectomized rats on a basic diet after two months, and (C) ovariectomized rats on a basic diet supplemented with Mg/Zn/F—CaP supplements after one month. FIG. 20 provides microCT images of femur head that demonstrate further the recovery in bone loss that may be achieved by providing a Mg/Zn/F—CaP dietary supplement. (A) is a microCT demonstrating the femur head of a rat on a basic diet, (B) is a microCT demonstrating bone loss in the femur head of a rat fed a mineral-deficient diet for two months, and (C) is a microCT demonstrating recovery of bone in the femur head of a rat fed a mineral-deficient diet for two months followed by a diet having a Mg/Zn/F—CaP dietary supplement for one month.

While the present invention has been described in terms of specific embodiments thereof, it will be understood in view of the present disclosure, that numerous variations upon the invention are now enabled to those skilled in the art. Accordingly, the invention is limited only by the scope and spirit of the claims appended.

The invention claimed is:

1. A biomaterial comprising a carbonate-containing calcium phosphate matrix comprising two or more phases, said matrix incorporating concentrations of magnesium, zinc, and fluorine ions.

2. A biomaterial in accordance with claim 1, wherein said matrix is biphasic and comprises carbonate hydroxyapatite (CHA) and β-tricalcium phosphate (β-TCP), said matrix incorporating concentrations of magnesium, zinc, and fluorine ions.

3. A biomaterial in accordance with claim 1, wherein Mg is present at 0.05 to 12 wt %, Zn is present at 0.01 to 12 wt % and F is present at 0.1 to 4 wt %, calcium is present at 20 to 40 wt %, phosphate (P) is present at 10 to 20 wt %, and carbonate ($CO_3$) is present at 1 to 20 wt %.

4. A biomaterial in accordance with claim 1, wherein Mg is present as 0.05 to 12 wt %.

5. A biomaterial in accordance with claim 1, wherein Zn is present as 0.01 to 12 wt %.

6. A biomaterial in accordance with claim 1, wherein F is present in an amount up to 4 wt %.

7. A biomaterial in accordance with claim 1 wherein the said material is particulate.

8. A biomaterial in accordance with claim 7, wherein the said material is highly sintered.

9. A biomaterial in accordance with claim 7, wherein said material is unsintered.

10. A biomaterial in accordance with claim 1 further comprising at least one ion selected from the group consisting of strontium, manganese, copper, boron and silicate.

11. A biomaterial in accordance with claim 1 further comprising at least one compound selected from the group consisting of a protein, a peptide and a nutraceutical.

12. A biomaterial in accordance with claim 1 further comprising at least one compound having antioxidant, anti-bacterial or anti-inflammatory properties.

13. A biomaterial in accordance with claim 1 wherein the biomaterial is a synthetic bone material.

* * * * *